(12) United States Patent
Megyese et al.

(10) Patent No.: US 11,761,940 B1
(45) Date of Patent: Sep. 19, 2023

(54) SYSTEMS AND METHODS FOR ENHANCING WATER SAFETY USING SENSOR AND UNMANNED VEHICLE TECHNOLOGIES

(71) Applicant: State Farm Mutual Automobile Insurance Company, Bloomington, IL (US)

(72) Inventors: Matthew Megyese, Phoenix, AZ (US); Sarah Ann Lockenvitz, Scottsdale, AZ (US); Paul Bates, Mesa, AZ (US); Nicholas Carmelo Marotta, Scottsdale, AZ (US); Cathy Jo Roth, Queen Creek, AZ (US); Austin Rowley, Mesa, AZ (US); Jared Wheet, Mesa, AZ (US)

(73) Assignee: State Farm Mutual Automobile Insurance Company, Bloomington, IL (US)

( * ) Notice: Subject to any disclaimer, the term of this patent is extended or adjusted under 35 U.S.C. 154(b) by 273 days.

(21) Appl. No.: 17/018,740

(22) Filed: Sep. 11, 2020

Related U.S. Application Data

(60) Provisional application No. 62/899,532, filed on Sep. 12, 2019.

(51) Int. Cl.
*G01N 33/18* (2006.01)
*G08B 21/12* (2006.01)
(Continued)

(52) U.S. Cl.
CPC ............. *G01N 33/18* (2013.01); *G01F 23/80* (2022.01); *G06Q 50/26* (2013.01); *G08B 21/12* (2013.01)

(58) Field of Classification Search
None
See application file for complete search history.

(56) References Cited

U.S. PATENT DOCUMENTS

| 3,762,214 A | 10/1973 | Bogusz |
| 4,685,158 A | 8/1987 | Lively |

(Continued)

FOREIGN PATENT DOCUMENTS

| CN | 108696833 A | 10/2018 |
| CN | 110779498 A | 2/2020 |

(Continued)

OTHER PUBLICATIONS

US 10,470,972 B2, 11/2019, Potucek et al. (withdrawn)

*Primary Examiner* — Paul M. West
*Assistant Examiner* — Mark A Shabman
(74) *Attorney, Agent, or Firm* — Armstrong Teasdale LLP

(57) ABSTRACT

A computer system including sensor technology for detecting environmental pollution levels in a water source and alerting users in real-time of the environmental pollution levels within the water source is provided. The computer system may be configured to receive pollution data from at least one sensor, analyze the received pollution data, and determine a level of environmental pollution in the water source based upon the analysis. The computer system may be also configured to determine, based upon the analysis of the pollution data, whether the water source is polluted, and generate an alert including information of the polluted water source. The computer system is further configured to generate a user list including at least one user of the water source, and transmit the alert to one or more client devices associated with the at least one user to notify the at least one user that the water source is polluted.

8 Claims, 9 Drawing Sheets

(51) Int. Cl.
 *G01F 23/80* (2022.01)
 *G06Q 50/26* (2012.01)

(56) References Cited

U.S. PATENT DOCUMENTS

| | | | |
|---|---|---|---|
| 6,676,831 | B2 | 1/2004 | Wolfe |
| 7,002,481 | B1 | 2/2006 | Crane et al. |
| 7,027,808 | B2 | 4/2006 | Wesby |
| 7,068,175 | B1 | 6/2006 | Pennington |
| 8,624,732 | B2 | 1/2014 | Hacek |
| 9,773,398 | B2 | 9/2017 | Abrahams et al. |
| 9,858,792 | B2 | 1/2018 | Fernandes et al. |
| 10,733,870 | B2 | 8/2020 | Aponte |
| 2002/0130069 | A1* | 9/2002 | Moskoff .............. G01N 33/18 422/50 |
| 2010/0300548 | A1 | 12/2010 | DeVerse |
| 2011/0011422 | A1 | 1/2011 | Jeon et al. |
| 2012/0174655 | A1* | 7/2012 | Essich .............. G01N 3/18 73/53.01 |
| 2012/0297028 | A1 | 11/2012 | Das et al. |
| 2015/0235545 | A1 | 8/2015 | Schoenheit et al. |
| 2016/0042629 | A1 | 2/2016 | Snyder |
| 2017/0352266 | A1 | 12/2017 | Watson |
| 2018/0165616 | A1 | 6/2018 | Sun et al. |
| 2019/0226898 | A1 | 7/2019 | Gray |
| 2019/0236732 | A1 | 8/2019 | Speasl et al. |

FOREIGN PATENT DOCUMENTS

| | | |
|---|---|---|
| CN | 210263154 U | 4/2020 |
| JP | 2012194738 A | 10/2012 |
| KR | 993248 B1 | 11/2010 |
| KR | 1933216 B1 | 12/2018 |
| WO | 1995026008 A1 | 9/1995 |
| WO | 2017127802 A1 | 7/2017 |

* cited by examiner

SYSTEMS AND METHODS FOR ENHANCING WATER SAFETY USING SENSOR AND UNMANNED VEHICLE TECHNOLOGIES

CROSS-REFERENCE TO RELATED APPLICATIONS

This application claims the benefit of priority to U.S. Provisional Patent Application Ser. No. 62/899,532, filed Sep. 12, 2019, entitled "SYSTEMS AND METHODS FOR ENHANCING WATER SAFETY USING SENSOR AND UNMANNED VEHICLE TECHNOLOGIES," the entire contents and disclosures of which are hereby incorporated herein by reference in its entirety.

FIELD OF THE INVENTION

The present disclosure relates to enhancing water safety and, more particularly, to network-based systems and methods for enhancing water safety using sensor and unmanned vehicle technologies.

BACKGROUND

Communities are concerned about safety of water used by members of said communities. In particular, communities are concerned about environmental pollution levels of local water sources, such as rivers and lakes, which may affect the quality of life of the members of these communities. Communities are also concerned about levels of local water sources, which may overflow causing floods that potentially damage property and injure the members of the communities. However, known systems may not accurately measure and detect environmental pollution levels in local water sources and/or flood risk areas leaving communities with uncertainty of the local water sources risks facing the members. Additionally, these known systems may not alert on time the members of the communities of their exposure to the imminent risks that local water sources may cause.

BRIEF SUMMARY

The present embodiments may relate to systems and methods for enhancing water safety using sensor and unmanned vehicle technologies. The system may include one or more user computing devices, one or more sensors, one or more unmanned vehicles (UVs), one or more insurance provider servers, third party computing systems, one or more client devices, and/or one or more databases.

In one aspect, a computer system including sensor technology for detecting environmental pollution levels in a water source and alerting users in real-time of the environmental pollution levels within the water source may be provided. The computer system may include at least one computing device including at least one processor and/or associated transceiver in communication with at least one memory device. The at least one processor and/or associated transceiver may be programmed to: (i) receive pollution data from at least one sensor, where the pollution data is gathered by the at least one sensor that is located at a water source, (ii) analyze the received pollution data, (iii) determine a level of environmental pollution in the water source based upon the analysis of the pollution data, (iv) determine, based upon the analysis of the pollution data, whether the water source is polluted, (v) in response to determining that the water source is polluted, generate an alert including information of the polluted water source, (vi) generate a user list including at least one user of the water source, and/or (vii) transmit the alert, via wireless communication or data transmission, to one or more client devices associated with the at least one user to notify the at least one user that the water source is polluted. The computer system may include additional, less, or alternate functionality, including that discussed elsewhere herein.

In another aspect, a computer system including sensor technology for detecting water levels in a water source and alerting users in real-time of the water levels of the water source may be provided. The computer system also includes at least one processor and/or associated transceiver in communication with at least one memory device. The at least one processor and/or associated transceiver may be programmed to: (i) receive water data from at least one sensor, where the water data is gathered by the at least one sensor located at a water source, (ii) analyze the received water data, (iii) determine one or more water levels of the water source based upon the analysis of the water data, (iv) determine, based upon the analysis of the water data, whether water is overflowing or at risk of overflowing the water source, (v) in response to determining water is overflowing or at risk of overflowing the water source, generate an alert including the one or more water levels of the water source, one or more locations where the water source is at risk of overflowing and/or where the water source is overflowed, (vi) generate a user list including at least one user of the water source, and/or (vii) transmit the alert, via wireless communication or data transmission, to one or more client devices associated with the at least one user to notify the at least one user that the water source is overflowing or at risk of overflowing. The computer system may include additional, less, or alternate functionality, including that discussed elsewhere herein.

In another aspect, a computer-implemented method for detecting environmental pollution levels in a water source and alerting users in real-time of the environmental pollution levels within the water source using a computer system including sensor technology may be provided. The computer system may include at least one computing device including at least one processor and/or associated transceiver in communication with at least one memory device. The method may include, via the at least one processor and/or associated transceiver: (i) receiving pollution data from at least one sensor, where the pollution data is gathered by the at least one sensor that is located at a water source, (ii) analyzing the received pollution data, (iii) determining a level of environmental pollution in the water source based upon the analysis of the pollution data, (iv) determining, based upon the analysis of the pollution data, whether the water source is polluted, (v) in response to determining that the water source is polluted, generating an alert including information of the polluted water source, (vi) generating a user list including at least one user of the water source, and/or (vii) transmitting the alert, via wireless communication or data transmission, to one or more client devices associated with the at least one user to notify the at least one user that the water source is polluted. The method may include additional, less, or alternate actions, including those discussed elsewhere herein.

In yet another aspect, a computer-implemented method for detecting water levels in a water source and alerting users in real-time of the water levels of the water source using a computer system including sensor technology may be provided. The computer system may include at least one computing device including at least one processor and/or associated transceiver in communication with at least one memory device. The method may include, via the at least one processor and/or associated transceiver: (i) receiving water data from at least one sensor, where the water data is gathered by the at least one sensor located at a water source, (ii) analyzing the received water data, (iii) determining one or more water levels of the water source based upon the analysis of the water data, (iv) determining, based upon the analysis of the water data, whether water is overflowing or at risk of overflowing the water source, (v) in response to determining water is overflowing or at risk of overflowing the water source, generating an alert including the one or more water levels of the water source, one or more locations where the water source is at risk of overflowing and/or where the water source is overflowed, (vi) generating a user list including at least one user of the water source, and/or (vii) transmitting the alert, via wireless communication or data transmission, to one or more client devices associated with the at least one user to notify the at least one user that the water source is overflowing or at risk of overflowing. The method may include additional, less, or alternate actions, including those discussed elsewhere herein.

Advantages will become more apparent to those skilled in the art from the following description of the preferred embodiments, which have been shown and described by way of illustration. As will be realized, the present embodiments may be capable of other and different embodiments, and their details are capable of modification in various respects. Accordingly, the drawings and description are to be regarded as illustrative in nature and not as restrictive.

BRIEF DESCRIPTION OF THE DRAWINGS

The Figures described below depict various aspects of the systems and methods disclosed therein. It should be understood that each Figure depicts an embodiment of a particular aspect of the disclosed systems and methods, and that each of the Figures is intended to accord with a possible embodiment thereof. Further, wherever possible, the following description refers to the reference numerals included in the following Figures, in which features depicted in multiple Figures are designated with consistent reference numerals.

There are shown in the drawings arrangements, which are presently discussed, it being understood, however, that the present embodiments are not limited to the precise arrangements and are instrumentalities shown, wherein.

Figure 1:
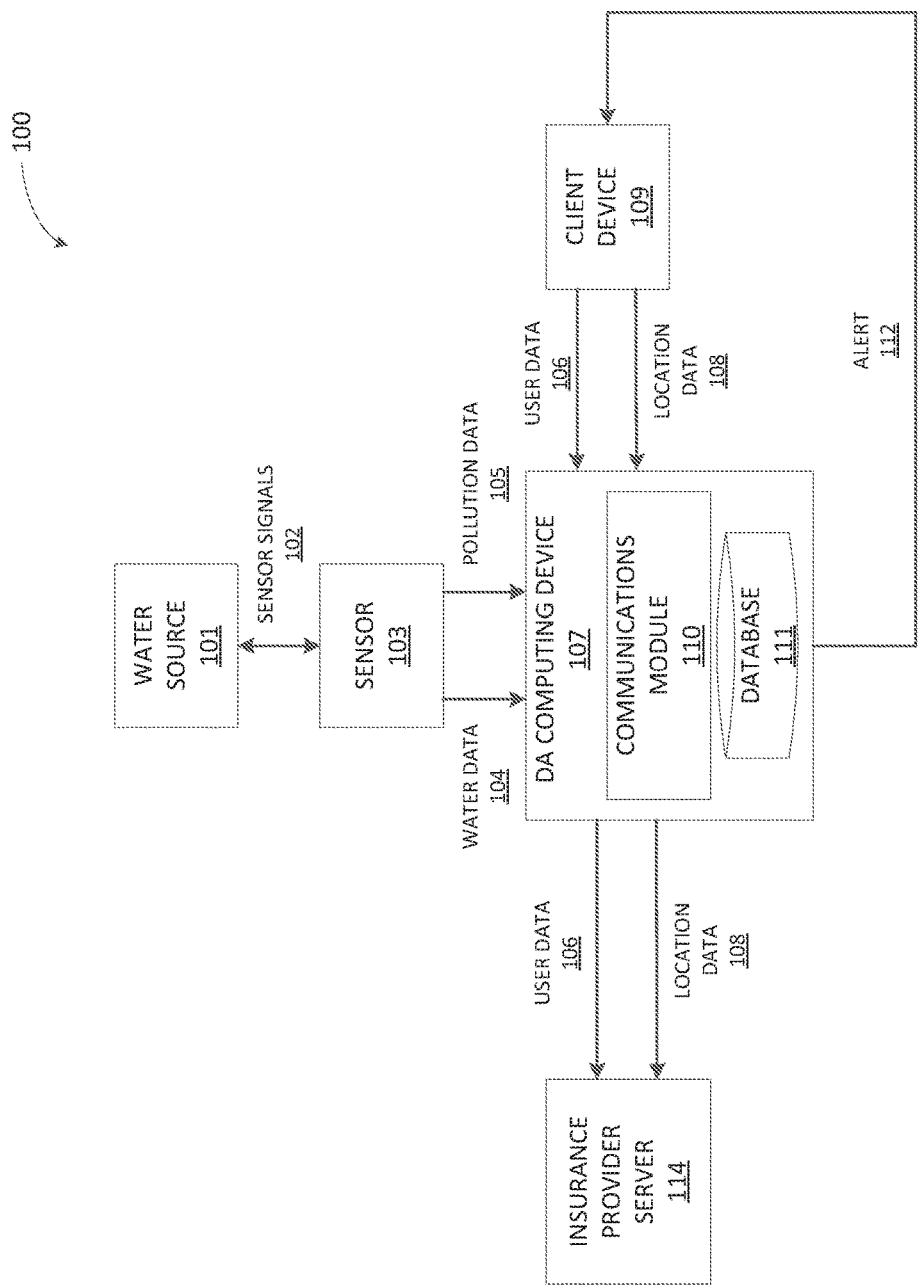
FIG. 1 illustrates a diagram of an exemplary computer system for detecting environmental pollution levels and water levels in a water source, and alerting users in real-time of the environmental pollution levels and the water levels within the water source.

The Figures depict preferred embodiments for purposes of illustration only. One skilled in the art will readily recognize from the following discussion that alternative embodiments of the systems and methods illustrated herein may be employed without departing from the principles of the invention described herein.

DETAILED DESCRIPTION

The present embodiments may relate to, inter alia, systems and methods for enhancing water safety using sensor and unmanned vehicle (UV) technologies. In particular, the systems and methods include a computer system configured to detect environmental pollution levels in water sources (e.g., lakes, rivers, and/or oceans) and the water levels of such water sources, and alert users (e.g., members of a community) in real-time of risks generated by the environmental pollution and water levels of the water sources. In at least one embodiment, the computer system may include a detection and alert (DA) computing device, at least one insurance provider server, at least one client device, one or more sensors, at least one UV, and a database. In other embodiments, the computer system may include a plurality of DA computing devices, insurance provider servers, client devices, sensors, UVs, and databases.

In the exemplary embodiment, the methods are performed by the DA computing device. The DA computing device may be in communication with the insurance provider server, the client device, the sensor, and the database. The DA computing device may be configured to receive sensor data (e.g., pollution level data (also referred herein as to pollution data) and/or water level data (also referred herein as to water data)) from the sensor. The sensors may include, but is not limited to, radar, LIDAR, Global Positioning System (GPS), video devices, imaging devices, cameras, audio recorders, and computer vision. The DA computing device may be also configured to retrieve the pollution data and the water data from the database, and/or store the pollution data and the water data within the database. The DA computing device may be further configured to receive topography data from the UV, and store and/or retrieve the topography data within/from the database. The UV may include, but is not limited to, an unmanned aerial vehicle (UAV) and/or an unmanned ground vehicle (UGV).

The DA computing device may be also configured to analyze the pollution data, the water data, and/or the topography data to determine risks (e.g., water pollution, floods) that users may be exposed, to generate an alert in real-time including the risks, and transmit the alert in real-time to client devices associated with the users. For example, the system may be able to send a boil water alert to a user if certain pollution parameters are met.

Client devices may be computers that include a web browser or a software application, which enables client devices to access remote computer devices, such as the DA computing device, using the Internet or other network. More specifically, the client devices may be communicatively coupled to the Internet through many interfaces including, but not limited to, at least one of a network, such as the Internet, a local area network (LAN), a wide area network (WAN), or an integrated services digital network (ISDN), a dial-up-connection, a digital subscriber line (DSL), a cellular phone connection, and a cable modem. Client devices may be any device capable of accessing the Internet including, but not limited to, a cellular phone, a smartphone, a tablet, a phablet, wearable electronics, smart watch, or other web-based connectable equipment or mobile devices.

In the exemplary embodiment, the sensor is located at a water source and generates the pollution data and the water data. In particular, the sensor or sensors may be configured to receive and/or transmit signals from/to the water source to generate the pollution data and the water data. In one example, the sensor may transmit signals to the water source and receive, in response to the transmission, signals that detect or measure, for example, a viscosity level of the water in the water source, and generate the pollution data including a pollution level of the water source.

Upon generating the pollution data, the sensor may transmit the pollution data to the DA computing device. In response to receiving the pollution data, the DA computing device may determine whether the water source is polluted. The DA computing device may use predefined thresholds (e.g., pollution thresholds) to make the determination. More specifically, the DA computing device may compare the information included in the pollution data to the predefined thresholds stored within the database. That is, the DA computing device may compare a water pollutant level to the predefined thresholds. Water pollutants may include contamination due to domestic wastes, insecticides and herbicides, food processing waste, pollutants from livestock operations, volatile organic compounds (VOCs), heavy metals, chemical waste, and other types of waste.

The DA computing device may determine that the water source is polluted if the water pollutant level meets, exceeds, or is below the predefined thresholds. In other words, the water pollutant level satisfies the pollution thresholds. In response to determining that the water source is polluted, the DA computing device may generate a user list including at least one user of the water source. The DA computing device may generate the user list based at least in part on user data previously received from the client devices associated with the at least one user.

The DA computing device may receive the user data in response to a user registering within the computer system and/or opting in to receive alerts. The user data for each user may include information of the user and the associated client device. Such information may include a user identifier, a client device identifier, a home address, a work address, a phone number, name(s) of the user, or the like. The DA computing device may use a location identifier included in the pollution data to parse and/or perform a lookup within the database for users of the water source, and identify in the user list the users of the water source.

In another example, the sensor may transmit signals to the water source and receive, in response to the transmission, signals detecting or measuring a water level in the water source. The sensors may also generate, using the received signals, water data including a level of the water in the water source. Upon generating the water data, the sensor may transmit the water data to the DA computing device. In response to receiving the water data, the DA computing device may determine whether the water source is overflowing or at risk of overflowing. A water source may be overflowing or at risk of overflowing has the water source has an excess or surplus of water that cannot be accommodated within the banks of the water source. The DA computing device may use predefined thresholds to make the determination.

More specifically, the DA computing device may compare the information included in the water data to the predefined thresholds stored within the database. The DA computing device may identify and/or retrieve, within or from the database, the predefined thresholds for a specific by performing a lookup for water levels recorded for the specific water source. For example, the DA computing device may compare the water level to the predefined thresholds stored within the database. The DA computing device may determine that the water source overflowed its banks or is about to overflow them if the water level meets, exceeds, or is below the predefined thresholds.

In response to determining that the water source is overflowing or at risk of overflowing, the DA computing device may generate a user list including at least one user of the water source. The DA computing device may receive the user data in response to a user registering within the computer system and/or opting in to receive alerts. The DA computing device may generate the user list based at least in part on user data previously received from the client devices associated with the at least one user, as discussed elsewhere herein. The DA computing device may use a location identifier included in the water data to parse the database to perform a lookup for users of the water source, and identify in the user list the users of the water source.

In the exemplary embodiment, the DA computing device may be configured to generate an alert in real-time once the users of the water source are identified based upon the pollution data and/or the water data. The DA computing device may link the alert to each identified user of the user list so that the DA computing device may transmit the alert in real-time to client devices associated with each identified user. The alert may include a notification indicating that the water source is polluted and/or its water level has caused or is about to cause a flooding. The alert may also include water quality alerts and boil water orders that may be transmitted by the DA computing device to client devices via a computer software application or a text message. The alert may also include directions indicating routes that users of the overflowed and/or polluted water source may use to travel to one or more safe locations (e.g., non-flooded locations) and/or safe water sources (e.g., non-polluted water sources). Once the DA computing device generates the alert, the DA computing device transmits the alert to the client devices associated with the identified users.

In certain embodiments, the DA computing device may be configured to determine whether communities or individual members of the communities are affected by polluted water sources using location data via a client software application stored on client devices associated with the individual members. For example, the DA computing device may receive from the software application stored on the client devices the location data including trips performed by the individual members of the communities who have the software application on their respective client devices.

The DA computing device may determine that these members are affected by polluted water sources in response to identifying locations, within the received location data, corresponding to previously identified non-polluted water sources. For example, if individual members of the communities frequent non-polluted water sources, the DA computing device may determine that these members are travelling to the non-polluted water sources in order to collect non-polluted water. In this example, the DA computing device may be configured to determine that members travelling to non-polluted water sources to collect non-polluted water require water commodity insurance coverage (e.g., reimbursement for trips to the non-polluted water sources). If the DA computing device determines that a member requires water commodity insurance coverage, the DA computing device transmits the location data and the user data associated with the member to one or more insurance servers so that an insurance provider associated with said servers may provide water commodity insurance coverage to the member.

In other embodiments, the DA computing device may use the location data in combination with the pollution data to determine whether communities or individual members of the communities are affected by polluted water sources. For example, if the pollution data from a water source do not meet a predefined threshold, but the DA computing device identifies, within the location data, destinations corresponding to safe water sources, the DA computing device may determine that the communities or the individual members are affected by polluted water sources, and thus the DA computing device may transmit the location data and the user data associated with the communities or the individual members to one or more insurance servers so that the insurance server may provide water commodity insurance coverage to the communities or the individual members.

In the exemplary embodiment, the DA computing device may be also configured to define flood risk areas (e.g., geographical areas at risk of flooding) based upon stored water data and topography data. Specifically, the DA computing device may be configured to determine areas prone to floods based upon the stored water data and/or a topography analysis of these areas. The stored water data may include flood information for these areas, such as, but not limited to, frequency of floods, level of the floods, and measurement of area covered by the floods.

The DA computing device may perform the topography analysis of these areas by analyzing topography data received from one or more UVs. The one or more UVs may be configured to transmit and/or receive UV signals to/from areas that may be at risk of flooding, and generate topography data. The topography data may include, but is not limited to, a water level state in these areas and imagery information including an arrangement of the natural and artificial features of these areas, such as elevation data, natural formation data (e.g., mountains, rivers, lakes), man-made formation data (e.g., roads, dams, buildings), slope data, and/or vegetation data.

The DA computing device may analyze the topography data by comparing the water level state to the imagery information. For example, the DA computing device may determine that an area which altitude is proximate to the water level of a riverbank (e.g., water level state) is more prone to floods compared to other areas located proximate to the meander of the river.

Once the DA computing device has determined the areas prone to flooding, the DA computing device may be configured to generate a geographical map identifying the flood risk zones. In some embodiments, the DA computing device may be in communication with one or more third party computing systems (e.g., a Federal Emergency Management Agency (FEMA) computing system, a National Weather Service computing system, or the like), which may transmit to the DA computing device flood information corresponding to a flood hazard mapping. In these embodiments, the DA computing device may use the received flood information to generate the geographical map identifying the flood risk zones.

In the exemplary embodiment, the DA computing device may be configured to store the geographical map within a database and link, using user data, the geographical map to users who reside in areas located within the geographical map. The DA computing device may also be configured to receive from the third party computing systems weather data (e.g., weather alerts) for areas included in the geographical map. The DA computing device may use information included in the weather alerts, such as precipitation level predictions, to determine the areas in the geographical map that are at risk of impending flooding. Once these areas are determined, the DA computing device may parse the database to perform a lookup for users located in the determined areas, generate an alert in real-time including information regarding the risk of impending flooding and directions indicating routes that the users may use to travel to one or more safe locations, and transmit the alert in real-time to client devices associated with the users.

In the exemplary embodiment, the DA computing device may be also configured to continuously update in real-time the records corresponding to the stored map using the received data from the sensors, the client devices the UVs, and/or the third party computing systems. By doing so, the DA computing device is enabled to predict floods in real-time using the most recent data, and thus generating virtually immediately and more accurate alerts compared to other computing systems, which may be slow and solely use stale data.

Additionally or alternatively, the DA computing device may be configured to determine water pollution levels that result from weather phenomena (e.g., rain, hail, and/or snow) by correlating water data to pollution data. In response to determining the pollution levels, the DA computing device may generate a visual graphical representation (e.g., a histogram, a pie chart, a regression analysis, or the like) illustrating the correlation between the water pollution levels and the weather phenomena. By performing this correlation, the DA computing device may generate alerts, such as the alerts discussed elsewhere herein, including risk of water pollution resulting from the weather phenomena.

In some embodiments, the DA computing device may be configured to monitor water levels in water sources, such as swimming pools, using one or more pool sensors comparable to the sensors used to monitor the water levels of water sources, such as lakes and rivers, as discussed elsewhere herein. The pool sensors may be located at the swimming pools and may be configured to generate and transmit water data to the DA computing device. In response to receiving the water data, the DA computing device may analyze the water data to determine whether water is leaking from the swimming pool or if overflows of water with the swimming pool are occurring possibly due to a water feed line being left on or accidentally being activated.

The DA computing device may use predefined thresholds to make the determination. More specifically, the DA computing device may compare the information included in the water data to the predefined thresholds, as discussed elsewhere herein with respect to water sources. In response to determining that water is leaking, at risk of overflowing, or overflowing the swimming pool, the DA computing device may parse the database to perform a lookup for one or more users of the swimming pool.

In one embodiment, the DA computing device may be configured to generate and transmit an alert to the one or more users indicating that water is leaking, at risk of overflowing, or overflowing the swimming pool so that the one or more users take action. In another embodiment, the DA computing device may generate and transmit the alert to the one or more users indicating that water is leaking, at risk of overflowing, or overflowing the swimming pool and the swimming pool will be automatically drained by the DA computing device. In this embodiment, the DA computing device may be in communication with a water depth controller of the swimming pool, which receives the draining instructions from the DA computing device that cause the water depth controller to drain the swimming pool.

Exemplary System for Detecting and Alerting of Environmental Pollution Levels and Water Levels in a Water Source FIG. 1 illustrates a diagram of an exemplary computer system 100 for detecting environmental pollution levels and water levels in a water source, and alerting users in real-time of the environmental pollution levels and the water levels within the water source. Computer system 100 may include detection and alert (DA) computing device 107, sensor 103, client device 109, insurance provider server 114, and database 111. Computer system 100 may also include a plurality of DA computing devices 107, sensors 103, client devices 109, databases 111, and insurance provider servers 114. In the exemplary embodiment, DA computing device 107 may be in communication, via communications module 110, with sensor 103, client device 109, database 111, and insurance provider server 114.

In the exemplary embodiment, sensor 103 may transmit and receive sensor signals 102 to/from water source 101. Water source 101 may include lakes, rivers, and/or oceans. Sensor 103 may generate water data 104 and pollution data 105 associated with water source 101 based upon sensor signals 102. Sensor 103 may also transmit water data 104 and pollution data 105 to DA computing device 107.

Client device 109 may generate user data 106 and location data 108 associated with the user and client device 109. Client device 109 may also transmit user data 106 and location data 108 to DA computing device 107. DA computing device 107 may be configured to store water data 104, pollution data 105, user data 106, and location data 108 within database 111.

DA computing device 107 may be also configured to retrieve water data 104, pollution data 105, user data 106, and location data 108 from database 111. In some embodiments, database 111 may be stored remotely from DA computing device 107. In other embodiments, database 111 may be decentralized.

Water data 104 may include at least a level of the water in water source 101, standing water data, ground saturation data, water-related natural formation data (e.g., rivers, lakes, and ponds) and received rain data. Pollution data 105 may include at least one of data of a water pollutant common to multiple water sources, data of a water pollutant specific to the location of water source 101, and data of illness in the local population due to a water pollutant. User data 106 may include information of the user and client device 109, such as a user identifier, a client device identifier, a home address, a work address, a phone number, name(s) of the user, or the like. Location data 108 may include tracking device information of client device 109, such as global position system (GPS) data, radio frequency identification (RFID) data, radio tracking data, and cell-phone triangulation data.

In the exemplary embodiment, sensor 103 may transmit a first set of sensor signals 102 to water source 101 and receive, in response to the transmission, a second set of sensor signals 102 detecting or measuring a water level in water source 101 and generate water data 104 including a level of the water in water source 101. Upon generating water data 104, sensor 103 may transmit water data 104 to DA computing device 107. In response to receiving water data 104, DA computing device 107 may determine whether water source 101 is overflowing or at risk of overflowing. DA computing device 107 may use predefined thresholds to make the determination.

More specifically, DA computing device 107 may compare the information included in water data 104 to the predefined thresholds. For example, DA computing device 107 may compare the water level to the predefined thresholds. DA computing device 107 may determine that water source 101 overflowed its banks or is about to overflow them if the water level meets, exceeds, or is below the predefined thresholds. In other words, the water pollutant level satisfies the pollution thresholds.

In response to determining that water source 101 is overflowing or at risk of overflowing, DA computing device 107 may generate a user list including at least one user of water source 101. DA computing device 107 may generate the user list based at least in part on user data 106 previously stored in database 111 and received from client devices 109 associated with the at least one user. User data 106 for each user may include information of the user and associated client device 109. DA computing device 107 may use a location identifier included in water data 104 to parse database 111 to perform a lookup for users of water source 101, and identify in the user list the users of water source 101.

In the exemplary embodiment, sensor 103 may also transmit a first set of sensor signals 102 to water source 101 and receive, in response to the transmission, a second set of sensor signals 102 detecting or measuring, for example, a viscosity level of the water in water source 101 and generate pollution data 105 including a pollution level of water source 101. Upon generating pollution data 105, sensor 103 may transmit pollution data 105 to DA computing device 107. In response to receiving pollution data 105, DA computing device 107 may determine whether the water source is polluted. DA computing device 107 may use predefined thresholds to make the determination.

More specifically, DA computing device 107 may compare the information included in pollution data 105 to the predefined thresholds. That is, DA computing device 107 may compare a water pollutant level to the predefined thresholds. DA computing device 107 may determine that water source 101 is polluted if the water pollutant level meets, exceeds, or is below the predefined thresholds.

In response to determining that water source 101 is polluted, DA computing device 107 may generate a user list including at least one user of water source 101. DA computing device 107 may generate the user list based at least in part on user data 106 previously stored in database 111 and received from client devices 109 associated with the at least one user. User data 106 for each user may include information of the user and associated client device 109. DA computing device 107 may use a location identifier included in pollution data 105 to parse and/or perform a lookup within database 111 for users of water source 101, and identify in the user list the users of water source 101.

In response to determining water source 101 is polluted, DA computing device 107 may generate alert 112 in real-time once the users of water source 101 are identified based upon pollution data 105 and/or the water data 104. DA computing device 107 may link alert 112 to each identified user of the user list so that DA computing device 107 may transmit alert 112 in real-time to client devices 109 associated with each identified user.

Alert 112 may include a notification indicating that water source 101 is polluted and/or its water level has caused or is about to cause a flooding. Alert 112 may also include water quality alerts and boil water orders that may be transmitted by DA computing device 107 to client devices 109 via a computer software application or a text message. A water quality alert may notify the users of poor water quality in water source 101 in order to caution users regarding use of water source 101. A boil water order may notify the users that any water obtained from water source 101 needs to be boiled, due to present pollution, in order to be safe for consumption. Alert 112 may also include directions indicating routes that users of the overflowed and/or polluted water source 101 may use to travel to one or more safe locations (e.g., non-flooded locations) and/or safe water sources (e.g., non-polluted water sources). Once DA computing device 112 generates alert 112, DA computing device 107 transmits alert 112 to client devices 109 associated with the identified users.

In an alternative embodiment, DA computing device 107 may analyze pollution data 105 from multiple water sources to determine a location of one or more safe water sources. DA computing device 107 may perform the analysis using predefined thresholds, as discussed elsewhere herein. In response to determining the location of the one or more safe water sources, DA computing device 107 may store the location as a safe water source within database 111. Client device 109 may transmit location data 108 to DA computing device 107, which may store location data 108 within database 111. DA computing device 107 may compare location data 108 and the location of the one or more safe water sources to determine the location of the closest safe water source from a user associated with client device 109. In response to determining the location of the closest safe water source, DA computing device 107 may transmit the determined location to client device 109 within alert 112 and/or a separate message from alert 112.

DA computing device 107 may be configured to use the location of the one or more safe water sources and location data 108 to determine whether the user as requiring water commodity insurance coverage. DA computing device 107 may make this determination by comparing predefined thresholds to the frequency that the user has travelled to the one or more safe water sources. If DA computing device 107 determines that the user requires water commodity insurance coverage, DA computing device 107 transmits location data 108 and user data 106 associated with the user to one or more insurance servers 114 so that insurance server 114 may provide water commodity insurance coverage to the user.

In other embodiments, DA computing device 107 may use location data 108 in combination with pollution data 105 to determine whether communities or individual users are affected by polluted water sources. For example, if pollution data 105 from water source 101 do not meet a predefined threshold, but DA computing device 107 identifies, within location data 108, destinations corresponding to safe water sources, DA computing device 107 may determine that the communities or the individual users are affected by polluted water sources, and thus DA computing device 107 may transmit location data 108 and user data 106 associated with the communities or the individual users to one or more insurance servers 114 so that insurance server 114 may provide water commodity insurance coverage to the communities or the individual users. Water commodity insurance coverage may determine the users as requiring insurance to cover at least one of the distance travelled and transportation used to obtain safe water due to pollution of water source 101.

Additionally or alternatively, DA computing device 107 may be configured to determine water pollution levels that result from weather phenomena (e.g., rain, hail, and/or snow) by correlating water data 104 to pollution data 105. In response to determining the pollution levels, DA computing device 107 may generate a visual graphical representation (e.g., a histogram, a pie chart, a regression analysis, or the like) illustrating the correlation between the water pollution levels and the weather phenomena. By performing this correlation, the DA computing device may generate alerts 112 including risk of water pollution resulting from the weather phenomena. Computer system 100 may include additional, less, or alternate functionality, including that discussed elsewhere herein.

Figure 2:
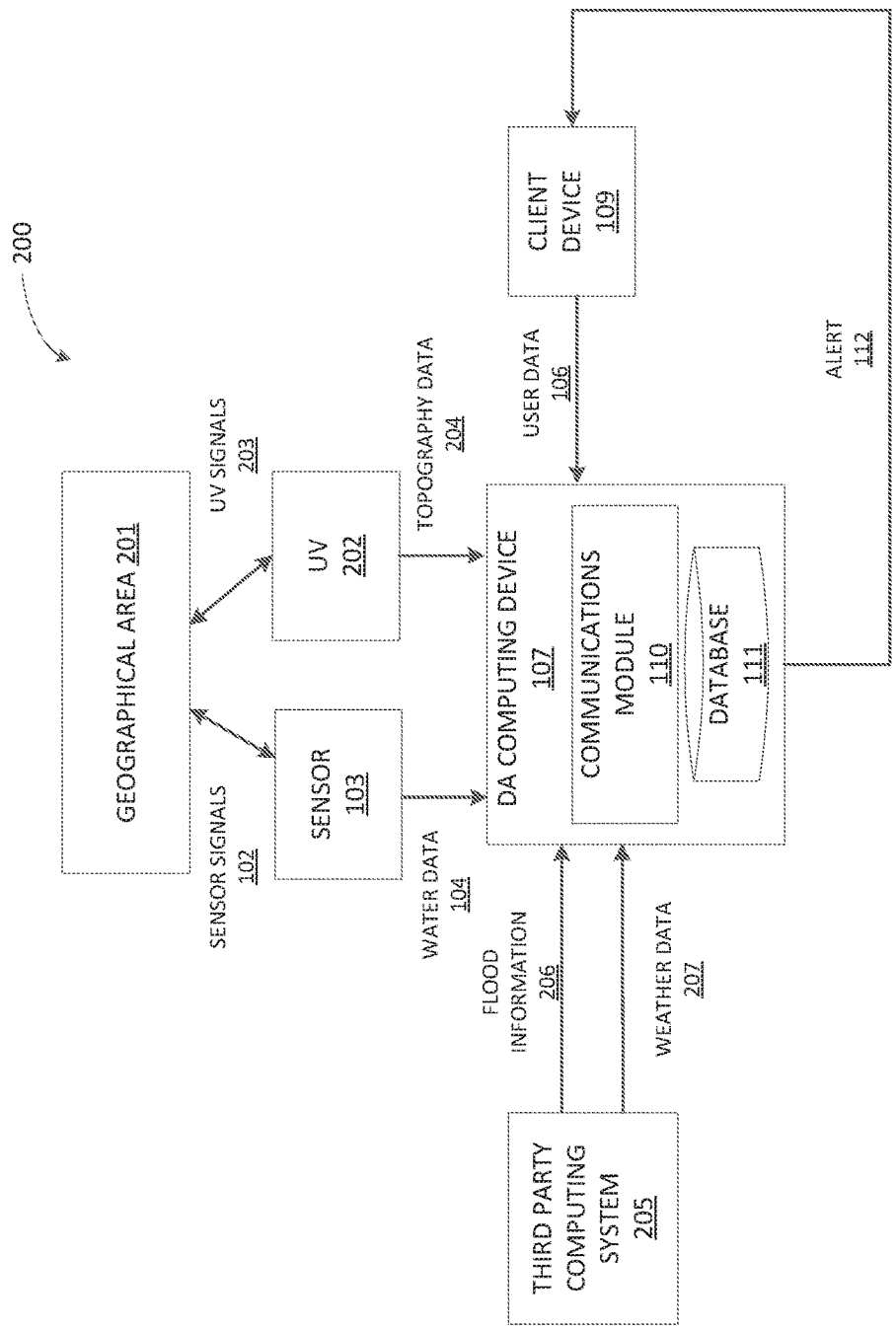
FIG. 2 illustrates a diagram of an exemplary computer system for identifying flood risk areas, identifying flood risk areas associated with water sources, and alerting users of impending flood risk areas.

Exemplary System for Identifying Flood Risks and Identifying Flood Risk Areas Associated with Water Sources FIG. 2 illustrates a diagram of an exemplary computer system 200 for identifying flood risk areas, identifying flood risk areas associated with water sources, and alerting users of impending flood risk areas. Computer system 200 may include detection and alert (DA) computing device 107, sensor 103, client device 109, insurance provider server 114, database 111, and unmanned vehicle (UV) 202. Computer system 200 may also include a plurality of DA computing devices 107, sensors 103, client devices 109, databases 111, insurance provider servers 114, and UVs 202. In the exemplary embodiment, DA computing device 107 may be in communication, via communications module 110, with sensor 103, client device 109, database 111, insurance provider server 114, UV 202, and one or more third party systems 205 (e.g., a Federal Emergency Management Agency (FEMA) computing system, a National Weather Service computing system, or the like).

In the exemplary embodiment, sensor 102 may receive and/or transmit sensor signals 102 from/to geographical area 201 and UV 202 may receive and/or transmit UV signals 203 from/to geographical area 201. Sensor 103 may generate water data 104 associated with geographical area 201 and transmit water level data 104 to DA computing device 107. UV 202 may generate topography data 204 associated with geographical area 201 and transmit topography data 204 to DA computing device 107. Topography data 204 may include, but not limited to, a water level state in geographical area 201 and imagery information including an arrangement of the natural and artificial features of geographical area 201, such as elevation data, natural formation data (e.g., mountains, rivers, lakes), manmade formation data (e.g., roads, dams, buildings), slope data, and/or vegetation data.

DA computing device may store water data 104 and topography data 204 within database 111. DA computing device 107 may also retrieve water data 104 and topography data 204 from database 111.

In some embodiments, geographical area 201 may be a geographical location of a varying size. For example, geographical area 201 may resemble areas such as a city, a mountain range, a basin, a field, and/or a forest. In addition, geographical area 201 may be, for example, for a size measured in inches, feet, miles, kilometers, and/or acres. In some embodiments, topography data 204 may be at least one of elevation data, natural formation data (e.g., mountains, rivers, and lakes), manmade formation data (e.g., roads, dams, and buildings), slope data, and/or vegetation data. In some embodiments, water level data may be at least one of standing water data, ground saturation data, water-related natural formation data (e.g., rivers, lakes, ponds), and received rain data.

In the exemplary embodiment, DA computing device 107 may be configured to define flood risk areas (e.g., geographical areas at risk of flooding) based upon stored water data 104 and topography data 204. Specifically, DA computing device 107 may be configured to determine geographical location 201 is prone to floods based upon stored water data 104 and/or a topography analysis of geographical location 201. Stored water data 104 may include flood information 206 for geographical location 201, such as, but not limited to, frequency of floods, level of the floods, and measurement of area covered by the floods. DA computing device 107 may perform the topography analysis of geographical location 201 by analyzing topography data 204 received from one or more UVs 202.

DA computing device 107 may analyze topography data 204 by comparing the water level state to the imagery information included in topography data 204. For example, DA computing device 107 may determine that geographical location 201 which altitude may be proximate to the water level of a riverbank (e.g., water level state) is more prone to floods compared to other geographical locations located proximate to the meander of the river.

Once DA computing device 107 has determined geographical location 201 is prone to floods, DA computing device 107 may be configured to generate a geographical map identifying the flood risk zones included in geographical location 201. In some embodiments, DA computing device 107 may be in communication with one or more third party computing systems 205, which may transmit to DA computing device 107 flood information 206 corresponding to a flood hazard mapping. In these embodiments, DA computing device 107 may use the received flood information 206 to generate the geographical map identifying the flood risk zones.

In the exemplary embodiment, DA computing device 107 may be configured to store the geographical map within database 111 and link, using user data 106, the geographical map to users who reside in areas located within the geographical map. DA computing device 107 may also be configured to receive from third party computing systems 205 weather data 207 (e.g., weather alerts) for areas included in the geographical map. DA computing device 107 may use information included in weather data 207, such as precipitation level predictions, to determine the areas in the geographical map that are at risk of impending flooding. Once these areas are determined, DA computing device 107 may parse database 111 to perform a lookup for users located in the determined areas, generate alert 112 in real-time including information regarding the risk of impending flooding and directions indicating routes that the users may use to travel to one or more safe locations, and transmit alert 112 in real-time to client devices 109 associated with the users.

In the exemplary embodiment, DA computing device 107 may be also configured to continuously update in real-time the records corresponding to the stored map using the received data from sensors 103, client devices 109, UVs 202, and/or third party computing systems 205. By doing so, DA computing device 107 is enabled to predict floods in real-time using the most recent data, and thus generating virtually immediately and more accurate alerts 112 compared to other computing systems, which may be slow and solely use stale data. Computer system 200 may include additional, less, or alternate functionality, including that discussed elsewhere herein.

Exemplary System for Monitoring and Controlling Swimming Pool Water Depth

Figure 3:
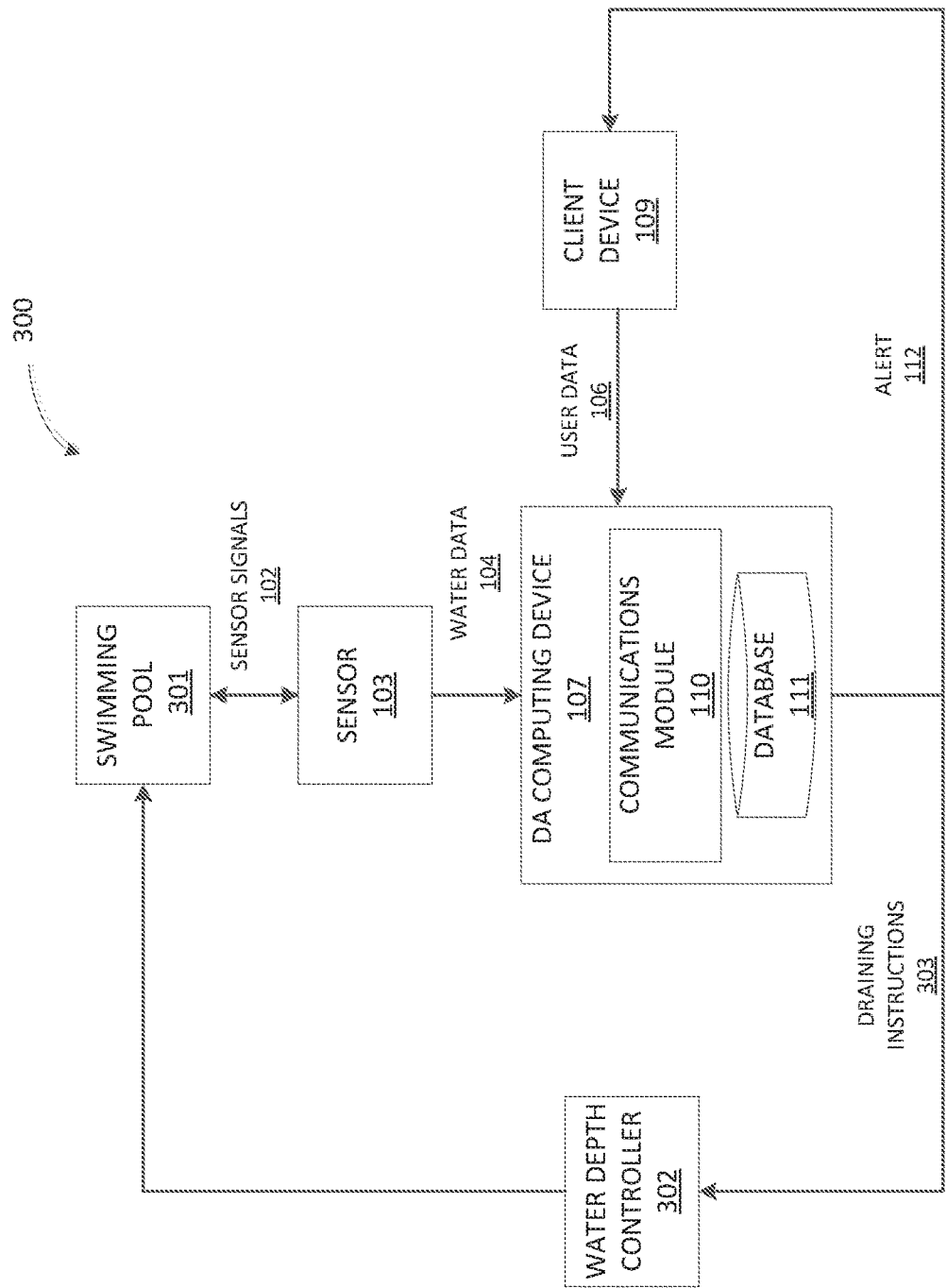
FIG. 3 illustrates a diagram of an exemplary computer system for monitoring and controlling water depth in a water source, such as a swimming pool.

FIG. 3 illustrates a diagram of an exemplary computer system 300 for monitoring and controlling swimming pool water depth. Computer system 300 may include detection and alert (DA) computing device 107, sensor 103, client device 109, insurance provider server 114, database 111, and water depth controller 302. Computer system 200 may also include a plurality of DA computing devices 107, sensors 103, client devices 109, databases 111, insurance provider servers 114, and water depth controllers 302. In the exemplary embodiment, DA computing device 107 may be in communication, via communications module 110, with sensor 103, client device 109, database 111, insurance provider server 114, and water depth controller 302.

In the exemplary embodiment, sensor 103 may be located at swimming pool 301 and may be configured to generate and transmit water data 104 to DA computing device 107. In response to receiving water data 104, DA computing device 107 may analyze water data 104 to determine whether water is leaking, at risk of overflowing, or overflowing swimming pool 301. DA computing device 107 may use predefined thresholds to make the determination. More specifically, DA computing device 107 may compare the information included in water data 104 to the predefined thresholds, as discussed elsewhere herein with respect to water sources. In response to determining that water is leaking, at risk of overflowing, or overflowing swimming pool 301, DA computing device 107 may parse database 111 to perform a lookup for one or more users of swimming pool 301. DA computing device 107 may perform the lookup using user data 106 previously stored in database 111 and received from client device 109 associated with one or more users of swimming pool 301.

In one embodiment, DA computing device 107 may be configured to generate and transmit alert 112 to the one or more users, via client device 109, indicating that water is leaking, at risk of overflowing, or overflowing swimming pool 301 so that the one or more users take action. In another embodiment, DA computing device 107 may generate and transmit alert 112 to the one or more users, via client device 109, indicating that water is leaking, at risk of overflowing, or overflowing swimming pool 301 and swimming pool 301 will be automatically drained by DA computing device 107. In this embodiment, DA computing device 107 may be in communication with water depth controller 302 of swimming pool 301, which receives draining instructions 303 from DA computing device 107 that cause water depth controller 302 to drain swimming pool 301. Computer system 300 may include additional, less, or alternate functionality, including that discussed elsewhere herein.

Exemplary Server Device

Figure 4:
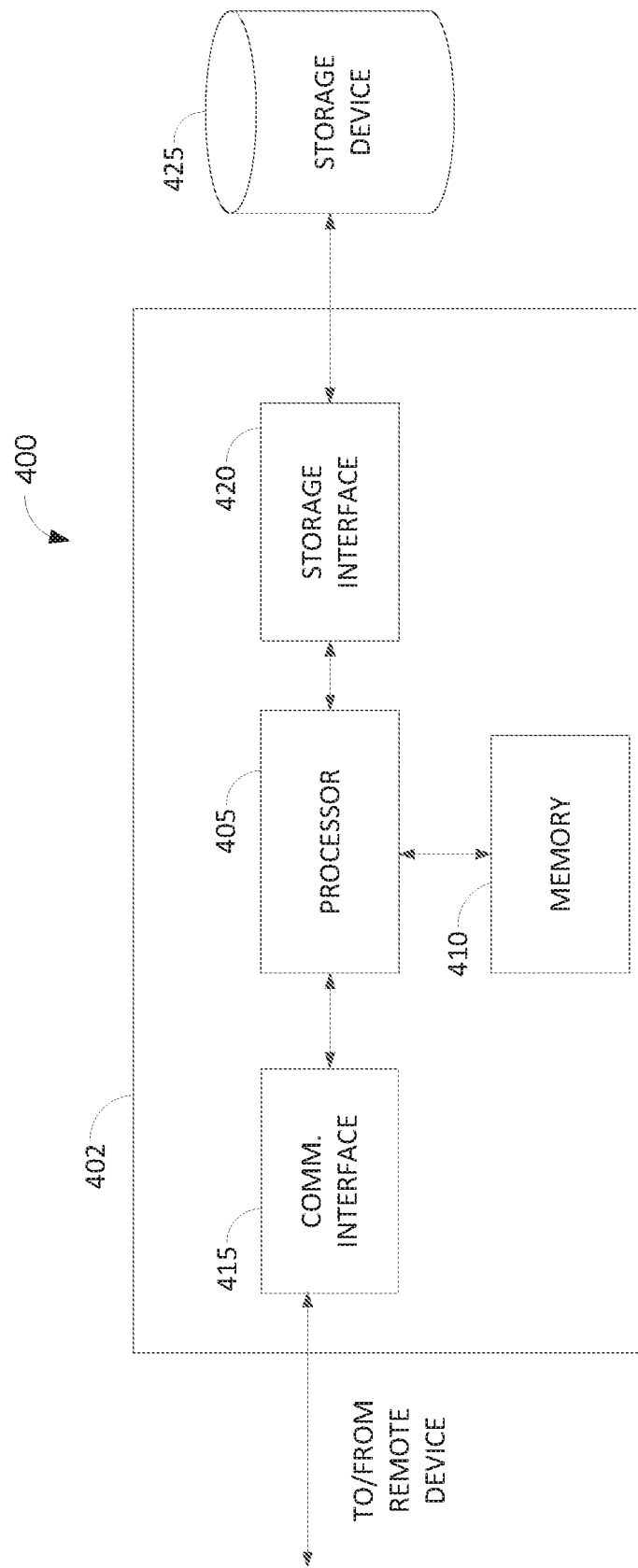
FIG. 4 depicts an exemplary configuration of an exemplary server computer device, in accordance with one embodiment of the present disclosure.

FIG. 4 depicts an exemplary configuration 400 of an exemplary server computer device 402, in accordance with one embodiment of the present disclosure. Server computer device 402 may include, but is not limited to, detection and alert (DA) computing device 107 (shown in FIGS. 1, 2, and 3), insurance provider server (shown in FIG. 1), and third party computing system 205 (shown in FIG. 2). Server computer device 402 may include a processor 405 for executing instructions. Instructions may be stored in a memory area 410. Processor 405 may include one or more processing units (e.g., in a multi-core configuration).

Processor 405 may be operatively coupled to a communication interface 415 such that server computer device 402 may be capable of communicating with a remote device such as another server computer device 402 or a user computing device, such as client device 109 (shown in FIGS. 1, 2, and 3). For example, communication interface 415 may receive requests from or transmit requests to client device 109 via the Internet.

Processor 405 may also be operatively coupled to a storage device 425. Storage device 425 may be any computer-operated hardware suitable for storing and/or retrieving data, such as, but not limited to, data associated with database 111 (shown in FIGS. 1, 2, and 3). In some embodiments, storage device 425 may be integrated in server computer device 402. For example, server computer device 402 may include one or more hard disk drives as storage device 425.

In other embodiments, storage device 425 may be external to server computer device 402 and may be accessed by a plurality of server computer devices 402. For example, storage device 425 may include a storage area network (SAN), a network attached storage (NAS) system, and/or multiple storage units such as hard disks and/or solid state disks in a redundant array of inexpensive disks (RAID) configuration.

In some embodiments, processor 405 may be operatively coupled to storage device 420 via a storage interface 420. Storage interface 420 may be any component capable of providing processor 405 with access to storage device 420. Storage interface 420 may include, for example, an Advanced Technology Attachment (ATA) adapter, a Serial ATA (SATA) adapter, a Small Computer System Interface (SCSI) adapter, a RAID controller, a SAN adapter, a network adapter, and/or any component providing processor 405 with access to storage device 420.

Processor 405 executes computer-executable instructions for implementing aspects of the disclosure. In some embodiments, processor 405 may be transformed into a special purpose microprocessor by executing computer-executable instructions or by otherwise being programmed.

Exemplary User Computer Device

Figure 5:
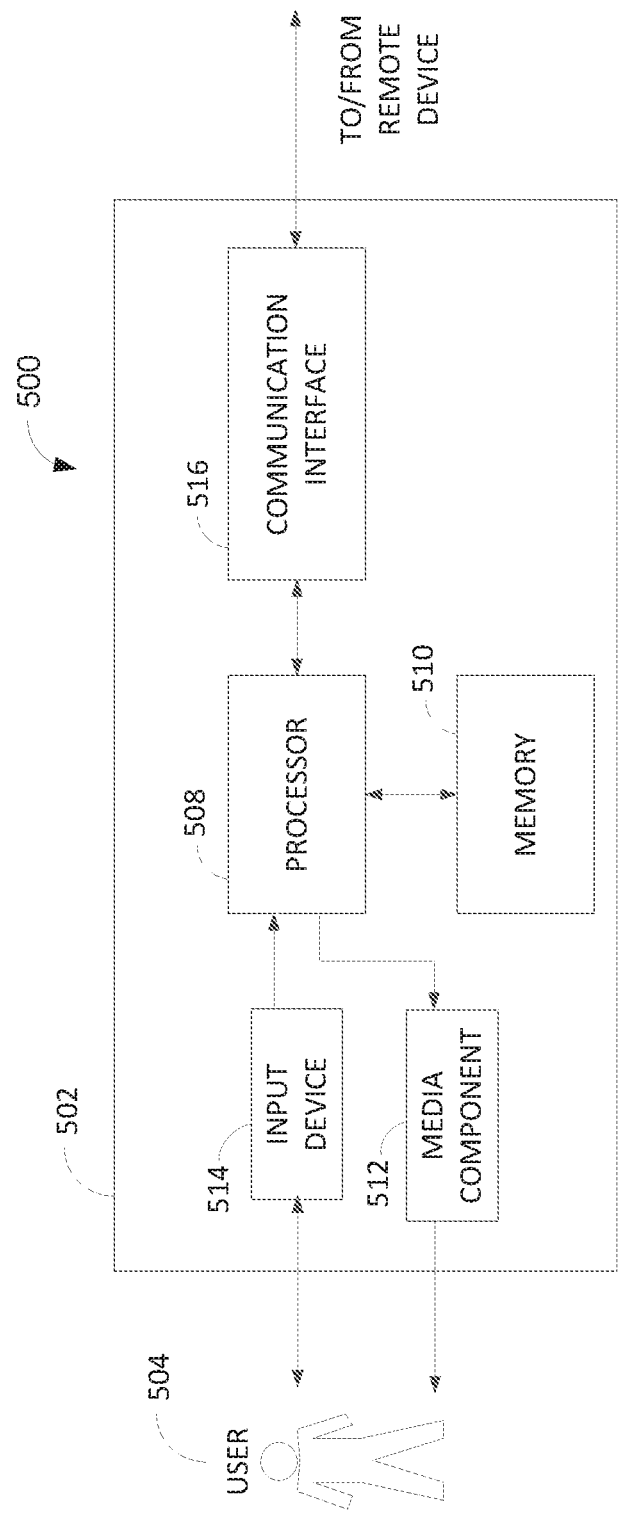
FIG. 5 illustrates an exemplary configuration of an exemplary user computing device

FIG. 5 illustrates an exemplary configuration 500 of an exemplary user computing device 502. In some embodiments, user computing device 502 may be in communication with a detection and alert (DA) computing device (such as DA computing device 107, shown in FIGS. 1, 2, and 3). User computing device 502 may be representative of, but is not limited to client device 109. For example, user computing device 502 may be a smartphone, tablet, smartwatch, wearable electronic, laptop, desktop, vehicle computing device, or another type of computing device associated with the account holder.

User computer device 502 may be operated by a user 504 to interact with DA computing device 107. User computer device 502 may receive input from user 504 via an input device 514. User computer device 502 includes a processor 508 for executing instructions. In some embodiments, executable instructions may be stored in a memory area 510. Processor 508 may include one or more processing units (e.g., in a multi-core configuration). Memory area 510 may be any device allowing information such as executable instructions and/or transaction data to be stored and retrieved. Memory area 510 may include one or more computer-readable media.

User computer device 502 also may include at least one media output component 512 for presenting information to user 504. Media output component 512 may be any component capable of conveying information to user 504. In some embodiments, media output component 512 may include an output adapter (not shown), such as a video adapter and/or an audio adapter. An output adapter may be operatively coupled to processor 508 and operatively coupleable to an output device, such as a display device (e.g., a cathode ray tube (CRT), liquid crystal display (LCD), light emitting diode (LED) display, or "electronic ink" display) or an audio output device (e.g., a speaker or headphones).

In some embodiments, media output component 512 may be configured to present a graphical user interface (e.g., a web browser and/or a client application) to user 504. A graphical user interface may include, for example, social insurance group activity, and/or a wallet application for managing payment information such as cash and/or cryptocurrency payment methods.

In some embodiments, user computer device 502 may include input device 514 for receiving input from user 504. User 504 may use input device 514 to, without limitation, interact with DA computing device 107 (e.g., using an app), or any of the computer devices discussed elsewhere herein. Input device 514 may include, for example, a keyboard, a pointing device, a mouse, a stylus, and/or a touch sensitive panel (e.g., a touch pad or a touch screen). A single component, such as a touch screen, may function as both an output device of media output component 512 and input device 514. User computer device 502 may further include at least one sensor, including, for example, a gyroscope, a position detector, a biometric input device, and/or an audio input device. In the exemplary embodiment, data collected by user computer device 502 may, but not limited to, include user data 106 (shown in FIGS. 1, 2, and 3) and/or location data 108 (shown in FIG. 1).

User computer device 502 may also include a communication interface 516, communicatively coupled to any of DA computing device 107, insurance provider server 114 (shown in FIG. 1), third party computing system 205 (shown in FIG. 2), and/or water depth controller 302 (shown in FIG. 3). Communication interface 516 may include, for example, a wired or wireless network adapter and/or a wireless data transceiver for use with a mobile telecommunications network.

Stored in memory area 510 may be, for example, computer-readable instructions for providing a user interface to user 504 via media output component 512 and, optionally, receiving and processing input from input device 514. The user interface may include, among other possibilities, a web browser, and/or a client application. Web browsers enable users, such as user 504, to display and interact with media and other information typically embedded on a web page or a website hosted by, for example, DA computing device 107. A client application may allow user 504 to interact with, for example, any of DA computing device 107, insurance provider server 114, third party computing system 205, and/or water depth controller 302. For example, instructions may be stored by a cloud service and the output of the execution of the instructions sent to the media output component 512.

Exemplary Embodiments and Functionality

Figure 6:
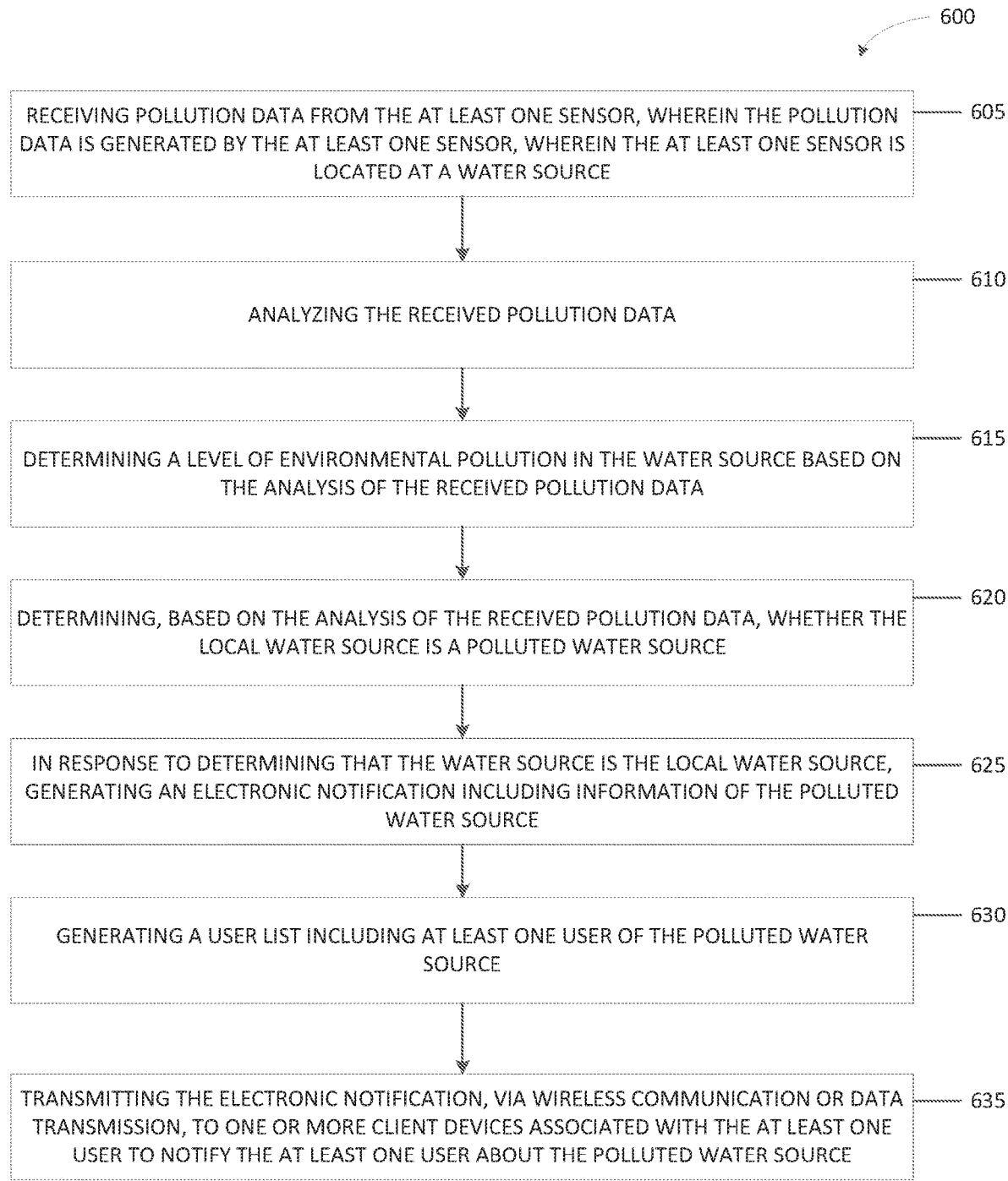
FIG. 6 illustrates a flow chart of an exemplary computer-implemented method for detecting environmental pollution levels in a water source and alerting users in real-time of the environmental pollution levels within the water source using the computer system shown in FIG. 1.

FIG. 6 illustrates a flow chart of an exemplary computer-implemented method 600 for detecting environmental pollution levels in a water source and alerting users in real-time of the environmental pollution levels within the water source using computer system 100 shown in FIG. 1. Method 600 may be implemented by a computing device, for example DA computing device 107 (shown in FIG. 1). In the exemplary embodiment, DA computing device 107 may be in communication with client device 109 (shown in FIG. 1).

In the exemplary embodiment, method 600 may include receiving 605 pollution data 105 from at least one sensor 103, where pollution data 105 is gathered by at least one sensor 103 that is located at a water source 101 (all shown in FIG. 1). Method 600 may also include analyzing 610 the received pollution data 105, determining 615 a level of environmental pollution in water source 101 based upon the analysis of pollution data 105, and determining 620, based upon the analysis of pollution data 105, whether water source 101 is polluted. Method 600 may further include determining whether water source 101 is polluted by comparing information in pollution data 105 to predefined thresholds. Method 600 may also include, in response to determining that water source 101 is polluted, generating 625 alert 112 (shown in FIG. 1) including information of polluted water source 101, and generating 630 a user list including at least one user of water source 101.

Method 600 may further include transmitting 635 alert 112, via wireless communication or data transmission, to one or more client devices 109 associated with the at least one user to notify the at least one user that water source 101 is polluted. Alert 112 may include, but is not limited to, an identification of the water source (e.g., name of the water source, location where the water source is polluted, etc.), a water quality alert, and/or a boil water order.

In addition, method 600 may include receiving location data 108 (shown in FIG. 1) from client device 109 associated with a user of water source 101. Client device 109 may be associated with at least one user of water source 101. Method 600 may also include identifying one or more safe water sources (e.g., non-polluted water sources) that are proximate to the user and/or one or more safe water sources where the user has travelled.

Method 600 may further include identifying the one or more safe water sources using location data 108 and pollution data 105 received from the safe water sources, where pollution data 105 does not meet the predefined thresholds, as discussed elsewhere herein. Method 600 may also include generating a safe water source list including a location of the identified one or more safe water sources. Method 600 may further include using the safe water source list to notify users of the polluted water about the location of safe water sources and/or identify users who are in need of commodity insurance coverage, as discussed elsewhere herein.

Figure 7:
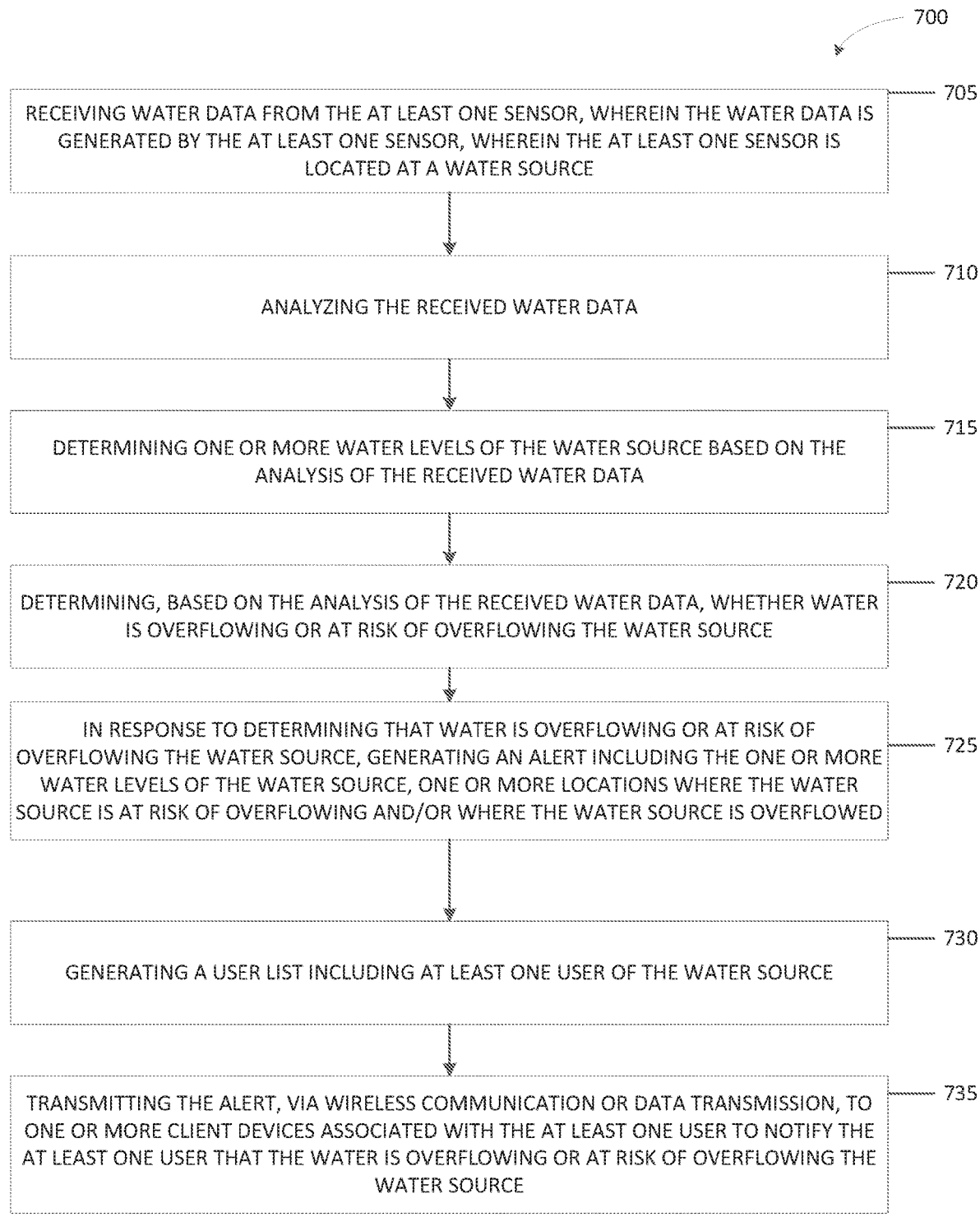
FIG. 7 illustrates a flow chart of an exemplary computer-implemented method for detecting water levels in a water source and alerting users in real-time of the water levels within the water source using the computer system shown in FIG. 1.

FIG. 7 illustrates a flow chart of an exemplary computer-implemented method 700 for detecting water levels in a water source and alerting users in real-time of the water levels within the water source using computer system 100 shown in FIG. 1. Method 700 may be implemented by a computing device, for example DA computing device 107 (shown in FIG. 1). In the exemplary embodiment, DA computing device 107 may be in communication with client device 109, and insurance provider server 114 (shown in FIG. 1).

In the exemplary embodiment, method 700 may include receiving 705 water data 104 from at least one sensor 103, where water data 104 gathered by at least one sensor 103 that is located at a water source 101 (all shown in FIG. 1). Method 700 may also include analyzing 710 the received water data 104, determining 715 a level of water in water source 101 based upon the analysis of water data 104, and determining 720, based upon the analysis of water data 104, whether water is overflowing or at risk of overflowing water source 101.

Method 700 may further include, in response to determining water is overflowing or at risk of overflowing water source 101, generating 725 alert 112 (shown in FIG. 1) including one or more water levels of water source 101, one or more locations where water source 101 is at risk of overflowing and/or where water source 101 is overflowed. Method 700 may also include generating 730 a user list including at least one user of water source 101.

Method 700 may further include transmitting 735 alert 112, via wireless communication or data transmission, to one or more client devices 109 associated with the at least one user to notify the at least one user that water source 101 is overflowing or at risk of overflowing. Alert 112 may include, but is not limited to, an identification of the water source (e.g., name of the water source, location where the water source is overflowing or at risk of overflowing, etc.), a water level of water source 101, safe areas (where there is no flooding or no risk of flooding) proximate to locations of users of water source 101, and/or routes/directions to these safe areas.

Figure 8:
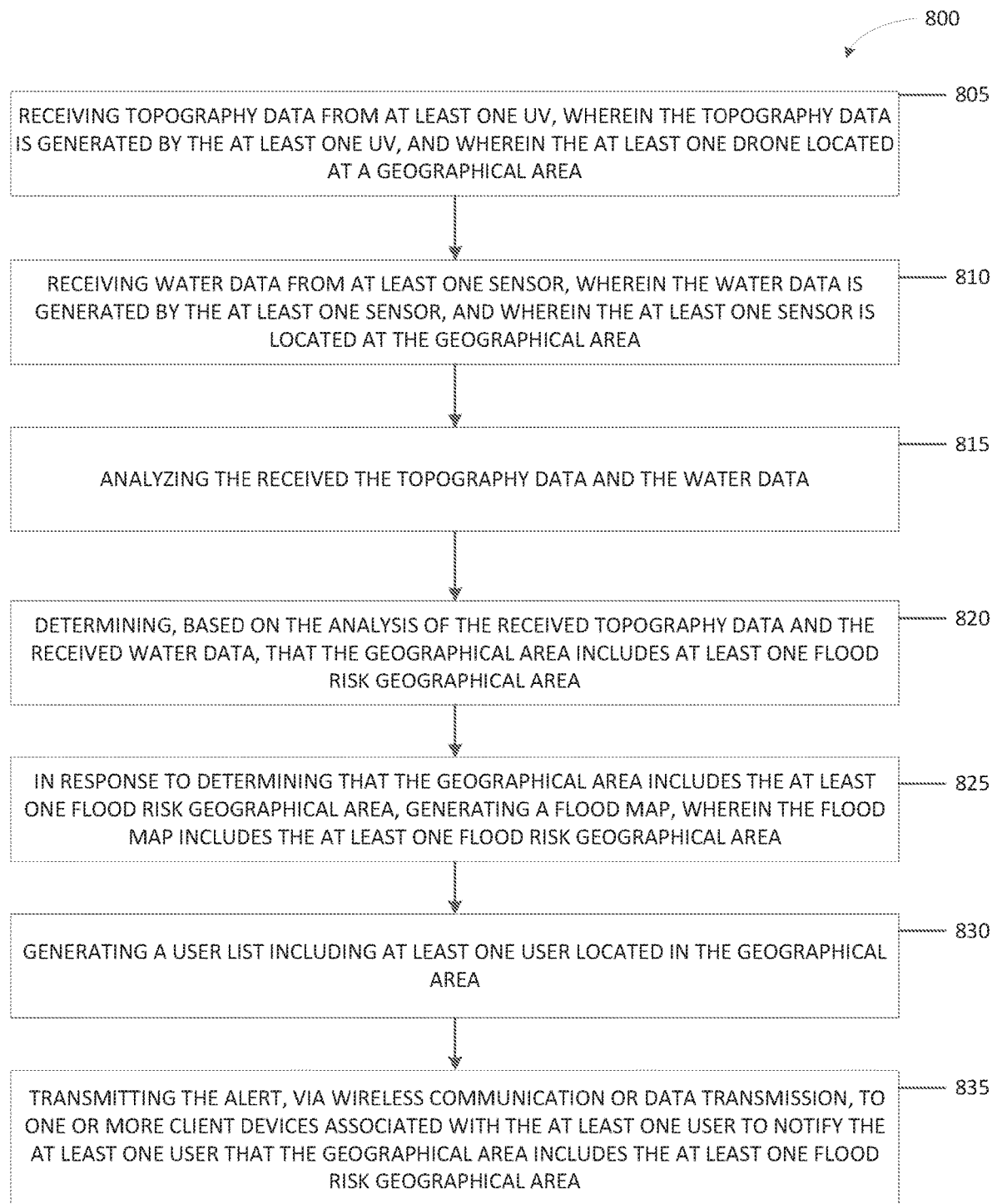
FIG. 8 illustrates a flow chart of an exemplary computer-implemented method for identifying a flood risk area using the computer system shown in FIG. 2.

FIG. 8 illustrates a flow chart of an exemplary computer-implemented method 800 for identifying a flood risk area using computer system 200 shown in FIG. 2. Method 800 may be implemented by a computing device, for example DA computing device 107 (shown in FIG. 2). In the exemplary embodiment, DA computing device 107 may be in communication with client device 109, sensor 103, unmanned vehicle (UV) 202, and third party computing system 205 (all shown in FIG. 2).

In the exemplary embodiment, method 800 may include receiving 805 topography data 204 of a geographical area 201 (both shown in FIG. 2) from at least one unmanned vehicle (UV), where geographical area 201 may include water source 101 (shown in FIG. 1). Topography data 204 may be gathered and/or generated by the at least one UV 202 that may be located at geographical area 201.

Method 800 may also include receiving 810 water data 104 (shown in FIG. 2) from sensor 103 located at geographical area 201. Water data 104 may be gathered by sensor 103. Method 800 may further include analyzing 815 the received water data 104 and topography data 204, and determining 820, based upon the analysis of the received water data 104 and topography data 204, whether geographical area 201 includes at least one flood risk geographical area.

Method 800 may further include, in response to determining that geographical area 201 includes at least one flood risk geographical area, generating 825 an alert 112 (shown in FIG. 2) including a flood map including the at least one flood risk geographical area. Method 800 may also include generating 830 a user list including at least one user located in geographical area 201. Method 800 may further include transmitting 835 alert 112, via wireless communication or data transmission, to one or more client devices 109 associated with the at least one user to notify the at least one user that geographical area 201 includes the at least one flood risk geographical area.

Figure 9:
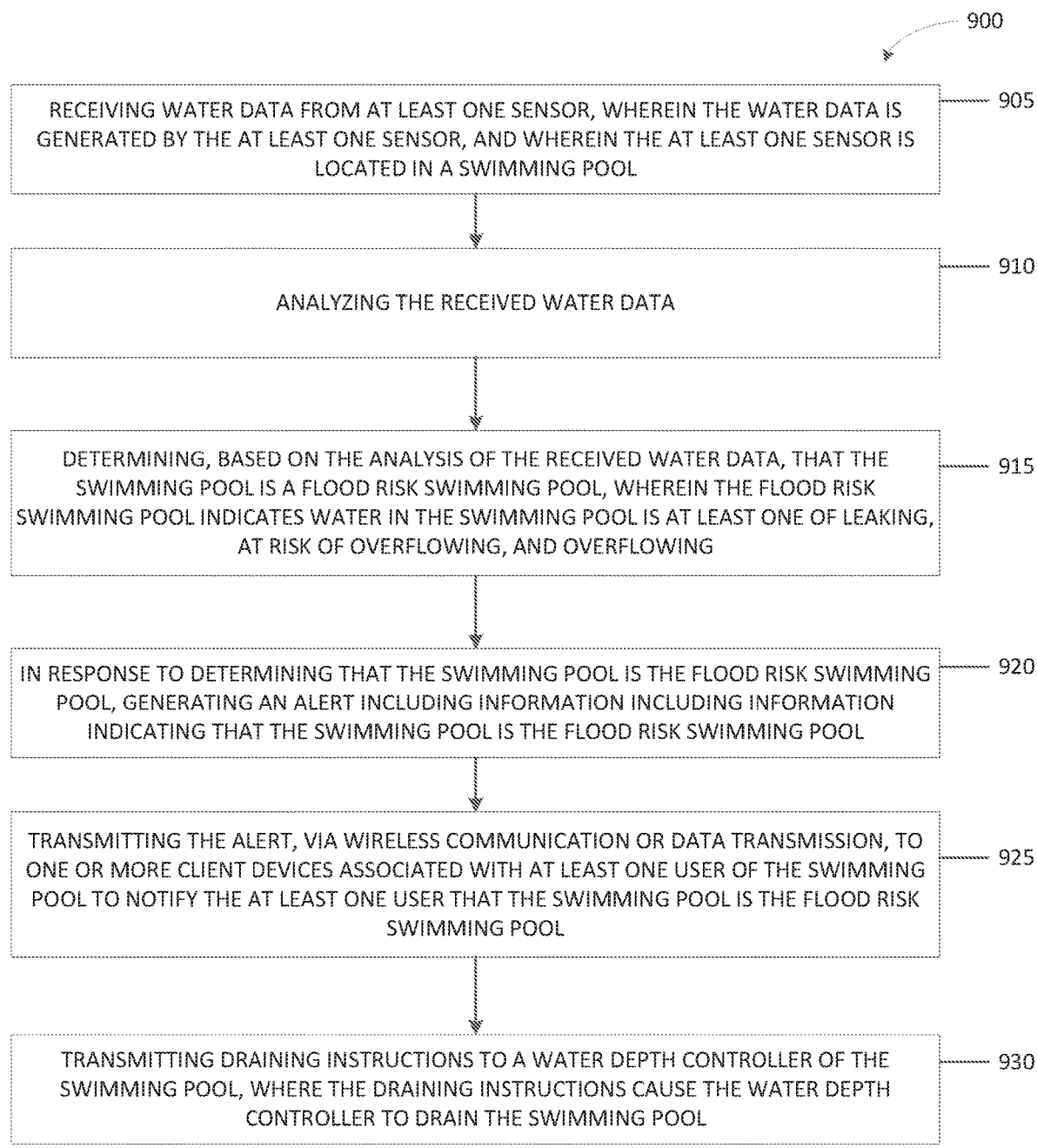
FIG. 9 illustrates a flow chart of an exemplary computer-implemented method for monitoring and controlling water depth within a water source, such as a swimming pool, using the computer system shown in FIG. 3.

FIG. 9 illustrates a flow chart of an exemplary computer-implemented method 900 for monitoring and controlling swimming pool water depth using computer system 300 shown in FIG. 3. Method 900 may be implemented by a computing device, for example DA computing device 107 (shown in FIG. 3). In the exemplary embodiment, DA computing device 107 may be in communication with client device 109, sensor 103, and water depth controller 302 (all shown in FIG. 3).

In the exemplary embodiment, method 900 may include receiving 905 water data from at least one sensor 103 (both shown in FIG. 3). Water data 104 may be gathered by at least one sensor 103 that may be located in swimming pool 301 (shown in FIG. 3). Method 900 may also include analyzing 910 the received water data 104, and determining 915, based upon the analysis of the received water data 104, whether swimming pool 301 is a flood risk swimming pool. A flood risk swimming pool may indicate that water is leaking, at risk of overflowing, or overflowing swimming pool 301.

Method 900 may further include, in response to determining that swimming pool 301 is the flood risk swimming pool, generating 920 an alert 112 (shown in FIG. 3) and/or notification including information indicating that swimming pool 301 is a flood risk swimming pool. The information included in alert 112 may include a water leak alert, at risk of water overflowing alert, or a water overflowing alert. Method 900 may also include transmitting 925 alert 112, via wireless communication or data transmission, to one or more client devices 109 associated with at least one user of swimming pool 301 to notify the at least one user that swimming pool 301 is a flood risk swimming pool.

Method 900 may further include transmitting 930 draining instructions 303 (shown in FIG. 3) to water depth controller 302 of swimming pool 302. Draining instructions 303 may include computer-executable instructions that cause water depth controller 302 to drain swimming pool 301. The computer systems discussed herein may include additional, less, or alternate functionality, including that discussed elsewhere herein Machine Learning & Other Matters The computer-implemented methods discussed herein may include additional, less, or alternate actions, including those discussed elsewhere herein. The methods may be implemented via one or more local or remote processors, transceivers, servers, and/or sensors, and/or via computer-executable instructions stored on non-transitory computer-readable media or medium.

Additionally, the computer systems discussed herein may include additional, less, or alternate functionality, including that discussed elsewhere herein. The computer systems discussed herein may include or be implemented via computer-executable instructions stored on non-transitory computer-readable media or medium.

A processor or a processing element may employ artificial intelligence and/or be trained using supervised or unsupervised machine learning, and the machine learning program may employ a neural network, which may be a convolutional neural network, a deep learning neural network, or a combined learning module or program that learns in two or more fields or areas of interest. Machine learning may involve identifying and recognizing patterns in existing data in order to facilitate making predictions for subsequent data. Models may be created based upon example inputs in order to make valid and reliable predictions for novel inputs.

Additionally or alternatively, the machine learning programs may be trained by inputting sample data sets or certain data into the programs, such as image data, text data, and/or numerical analysis. The machine learning programs may utilize deep learning algorithms that may be primarily focused on pattern recognition, and may be trained after processing multiple examples. The machine learning programs may include Bayesian program learning (BPL), voice recognition and synthesis, image or object recognition, optical character recognition, and/or natural language processing—either individually or in combination. The machine learning programs may also include natural language processing, semantic analysis, automatic reasoning, and/or machine learning.

In supervised machine learning, a processing element may be provided with example inputs and their associated outputs, and may seek to discover a general rule that maps inputs to outputs, so that when subsequent novel inputs are provided the processing element may, based upon the discovered rule, accurately predict the correct output. In unsupervised machine learning, the processing element may be required to find its own structure in unlabeled example inputs. In one embodiment, machine learning techniques may be used to extract data about the computer device, the user of the computer device, driver and/or vehicle, documents to be provided, the model being simulated, home owner and/or home, buyer, geolocation information, image data, home sensor data, and/or other data.

Based upon these analyses, the processing element may learn how to identify characteristics and patterns that may then be applied to training models, analyzing sensor data, authentication data, image data, mobile device data, and/or other data.

Exemplary Embodiments

In one embodiment, a computer system including sensor technology for detecting environmental pollution levels in a water source and alerting users in real-time of the environmental pollution levels within the water source may be provided. The computer system may include at least one computing device including at least one processor and/or associated transceiver in communication with at least one memory device. The at least one processor and/or associated transceiver may be programmed to: (i) receive pollution data from at least one sensor, where the pollution data is gathered by the at least one sensor that is located at a water source, (ii) analyze the received pollution data, (iii) determine a level of environmental pollution in the water source based upon the analysis of the pollution data, (iv) determine, based upon the analysis of the pollution data, whether the water source is polluted, (v) in response to determining that the water source is polluted, generate an alert including information of the polluted water source, (vi) generate a user list including at least one user of the water source, and/or (vii) transmit the alert, via wireless communication or data transmission, to one or more client devices associated with the at least one user to notify the at least one user that the water source is polluted. The computer system may include additional, less, or alternate functionality, including that discussed elsewhere herein.

For example, the alert may be at least one of a water quality alert and a boil water order. Further, the at least one processor and/or associated transceiver may be programmed to: (i) receive location data associated with the at least one user, (ii) generate a safe water source list including a location of at least one safe water source, wherein the at least one local safe water source is not the polluted water source, (iii) compare the received location data associated with the at least one user and the location of the at least one safe water source, (iv) determine, based upon the comparison, whether the at least one user is travelling to the at least one safe water source, (v) in response to determining that the at least one user is travelling to the at least one safe water source, determine that the at least one user requires a water commodity insurance coverage, (vi) store, in the at least one memory device, the received pollution data from the at least one sensor, and/or (vii) store, in the at least one memory device, the user list including the at least one user of the polluted water source.

In another embodiment, a computer system including sensor technology for detecting water levels in a water source and alerting users in real-time of the water levels of the water source may be provided. The computer system also includes at least one processor and/or associated transceiver in communication with at least one memory device. The at least one processor and/or associated transceiver may be programmed to: (i) receive water data from at least one sensor, where the water data is gathered by the at least one sensor located at a water source, (ii) analyze the received water data, (iii) determine one or more water levels of the water source based upon the analysis of the water data, (iv) determine, based upon the analysis of the water data, whether water is overflowing or at risk of overflowing the water source, (v) in response to determining water is overflowing or at risk of overflowing the water source, generate an alert including the one or more water levels of the water source, one or more locations where the water source is at risk of overflowing and/or where the water source is overflowed, (vi) generate a user list including at least one user of the water source, and/or (vii) transmit the alert, via wireless communication or data transmission, to one or more client devices associated with the at least one user to notify the at least one user that the water source is overflowing or at risk of overflowing. The computer system may include additional, less, or alternate functionality, including that discussed elsewhere herein.

For example, the at least one processor may be further configured to: (i) generate a user list including at least one user of the water source, (ii) generate the user list based at least in part on user data previously received from the one or more client devices associated with the at least one user, (iii) compare the water data to predefined thresholds stored within the at least one memory device, and/or (iv) determine, based upon the comparison, whether water is at least one of overflowing and at risk of overflowing the water source.

In another embodiment, a computer system including sensor and unmanned vehicle (UV) technologies for identifying a flood risk area may be provided. The computer system may include at least one processor and/or associated transceiver in communication with at least one memory device. The at least one processor and/or associated transceiver may be programmed to: (i) receive topography data of a geographical area from at least one UV, where the topography data may be gathered and/or generated by the at least one UV that may be located at the geographical area, (ii) receive water data from at least one sensor located at the geographical area, where the water data may be gathered by the at least one sensor, (iii) analyze the received water data and topography data, (iv) determine, based upon the analysis of the received water data and topography data, that the geographical area includes at least one flood risk geographical area, (v) in response to determining that the geographical area includes the at least one flood risk geographical area, generate an alert including a flood map including the at least one flood risk geographical area, (vi) generate a user list including at least one user located in the geographical area, and/or (vii) transmit the alert, via wireless communication or data transmission, to one or more client devices associated with the at least one user to notify the at least one user that the geographical area includes the at least one flood risk geographical area. The computer system may include additional, less, or alternate functionality, including that discussed elsewhere herein.

For example, the at least one processor may further be configured to: (i) generate a user list including the at least one user located in the geographical area, (ii) store, in the at least one memory device, the received topography data from the at least one UV, (iii) receive location data associated with the at least one flood risk geographical area, (iv) generate a location of the at least one flood risk geographical area based upon the received location data, (v) receive, from a third party computing system, weather data associated with the location of the at least one flood risk geographical area, and/or (vi) determine, within the at least one flood risk geographical area, one or more areas being at an impending flood risk level based upon the weather data. Further, transmitting the alert may further comprise including a notification indicating the impending flood risk level of the one or more areas.

In another embodiment, a computer system including sensor technology for monitoring and controlling swimming pool water depth may be provided. The computer system may include at least one processor and/or associated transceiver in communication with at least one memory device. The at least one processor and/or associated transceiver may be programmed to: (i) receive water data from at least one sensor, where the water data may be gathered by the at least one sensor that may be located in a swimming pool, (ii) analyze the received water data, (iii) determine, based upon the analysis of the received the water data, that the swimming pool is a flood risk swimming pool, where the flood risk swimming pool includes a threshold amount of water leaking from the swimming pool or a threshold amount of water overflowing the swimming pool, (iv) generate an alert including information indicating that the swimming pool is a flood risk swimming pool, (v) transmit the alert, via wireless communication or data transmission, to one or more client devices associated with at least one user of the swimming pool to notify the at least one user that the swimming pool is a flood risk swimming pool, and/or (vi) transmit draining instructions to a water depth controller of the swimming pool, where the draining instructions cause the water depth controller to drain the swimming pool. The computer system may include additional, less, or alternate functionality, including that discussed elsewhere herein.

For example, the alert may include at least one of a water leak alert, at risk of water overflowing alert, and a water overflowing alert. Further, the at least one processor may be configured to: (i) store, in the at least one memory device, the received water data from the at least one sensor and/or (ii) transmit draining instructions to a water depth controller of the swimming pool, wherein the draining instructions cause the water depth controller to drain the swimming pool.

In another embodiment, a computer-implemented method for detecting environmental pollution levels in a water source and alerting users in real-time of the environmental pollution levels within the water source using a computer system including sensor technology may be provided. The computer system may include at least one computing device including at least one processor and/or associated transceiver in communication with at least one memory device. The method may include, via the at least one processor and/or associated transceiver: (i) receiving pollution data from at least one sensor, where the pollution data is gathered by the at least one sensor that is located at a water source, (ii) analyzing the received pollution data, (iii) determining a level of environmental pollution in the water source based upon the analysis of the pollution data, (iv) determining, based upon the analysis of the pollution data, whether the water source is polluted, (v) in response to determining that the water source is polluted, generating an alert including information of the polluted water source, (vi) generating a user list including at least one user of the water source, and/or (vii) transmitting the alert, via wireless communication or data transmission, to one or more client devices associated with the at least one user to notify the at least one user that the water source is polluted. The method may include additional, less, or alternate actions, including those discussed elsewhere herein.

For example, the alert may be at least one of a water quality alert and a boil water order. Further, the method may further include: (i) receiving, via the at least one processor and/or associated transceiver, location data associated with the at least one user, (ii) generating, via the at least one processor, a safe water source list including a location of at least one safe water source, wherein the at least one local safe water source is not the polluted water source, (iii) comparing, via the at least one processor, the received location data associated with the at least one user and the location of the at least one safe water source, (iv) determining based upon the comparison, via the at least one processor, whether the at least one user is travelling to the at least one safe water source, (v) in response to determining that the at least one user is travelling to the at least one safe water source, determining, via the at least one processor, that the at least one user requires a water commodity insurance coverage, (vi) storing in the at least one memory device, via the at least one processor, the received pollution data from the at least one sensor, and/or (vii) storing in the at least one memory device, via the at least one processor, the user list including the at least one user of the polluted water source.

In another embodiment, a computer-implemented method for detecting environmental pollution levels in a water source and alerting users in real-time of the environmental pollution levels within the water source may be provided. The method may be implemented via a computer system including at least one processor and/or associated transceiver in communication with at least one memory device and at least one sensor. The method may include: (i) receiving, via the at least one processor and/or associated transceiver, pollution data from at least one sensor, wherein the pollution data is gathered by the at least one sensor located at a water source, (ii) determining, via the at least one processor, a level of environmental pollution in the water source based upon the received pollution data, (iii) determining, via the at least one processor, based upon the analysis of the pollution data, whether the water source is polluted, (iv) in response to determining that the water source is polluted, generating, via the at least one processor, an alert including information corresponding to the polluted water source, (v) generating, via the at least one processor, a user list including at least one user of the water source, and/or (vi) transmitting, via the at least one processor and/or associated transceiver, the alert, via wireless communication or data transmission, to one or more client devices associated with the at least one user to notify the at least one user that the water source is polluted. The method may include additional, less, or alternate actions, including those discussed elsewhere herein.

For example, the alert may be at least one of a water quality alert and a boil water order. The method may further include: (i) receiving, via the at least one processor and/or associated transceiver, location data associated with the at least one user, (ii) generating, via the at least one processor, a safe water source list including a location of at least one safe water source, wherein the at least one local safe water source is not the polluted water source, (iii) comparing, via the at least one processor, the received location data associated with the at least one user and the location of the at least one safe water source, (iv) determining based upon the comparison, via the at least one processor, whether the at least one user is travelling to the at least one safe water source, (v) in response to determining that the at least one user is travelling to the at least one safe water source, determining, via the at least one processor, that the at least one user requires a water commodity insurance coverage, (vi) storing in the at least one memory device, via the at least one processor, the received pollution data from the at least one sensor, and/or (vii) storing in the at least one memory device, via the at least one processor, the user list including the at least one user of the polluted water source.

In yet another aspect, a computer-implemented method for detecting water levels in a water source and alerting users in real-time of the water levels of the water source using a computer system including sensor technology may be provided. The computer system may include at least one computing device including at least one processor and/or associated transceiver in communication with at least one memory device. The method may include, via the at least one processor and/or associated transceiver: (i) receiving water data from at least one sensor, where the water data is gathered by the at least one sensor located at a water source, (ii) analyzing the received water data, (iii) determining one or more water levels of the water source based upon the analysis of the water data, (iv) determining, based upon the analysis of the water data, whether water is overflowing or at risk of overflowing the water source, (v) in response to determining water is overflowing or at risk of overflowing the water source, generating an alert including the one or more water levels of the water source, one or more locations where the water source is at risk of overflowing and/or where the water source is overflowed, (vi) generating a user list including at least one user of the water source, and/or (vii) transmitting the alert, via wireless communication or data transmission, to one or more client devices associated with the at least one user to notify the at least one user that the water source is overflowing or at risk of overflowing. The method may include additional, less, or alternate actions, including those discussed elsewhere herein.

For example, the computer-implemented method may further include: (i) generating, via the at least one processor, a user list including at least one user of the water source, (ii) generating, via the at least one processor, the user list based at least in part on user data previously received from the one or more client devices associated with the at least one user, (iii) comparing, via the at least one processor, the water data to predefined thresholds stored within the at least one memory device, and/or (iv) determining based upon the comparison, via the at least one processor, whether water is at least one of overflowing and at risk of overflowing the water source.

In another embodiment, a computer-implemented method for identifying a flood risk area, the method being implemented via computer system including at least one processor and/or associated transceiver in communication with at least one memory device, at least one unmanned vehicle (UV), and at least one sensor may be provided. The method may include: (i) receiving, via the at least one processor and/or associated transceiver, topography data of a geographical area from at least one unmanned vehicle (UV), wherein the topography data is generated by the at least one UV located at the geographical area, (ii) receiving, via the at least one processor and/or associated transceiver, water data from at least one sensor located at the geographical area, wherein the water data is generated by the at least one sensor, (iii) determining based upon the received water data and topography data, via the at least one processor, that the geographical area includes at least one flood risk geographical area, (iv) in response to determining that the geographical area includes the at least one flood risk geographical area, generating, via the at least one processor, an alert including a flood map including the at least one flood risk geographical area, and/or (v) transmitting, via the at least one processor and/or associated transceiver, the alert, via wireless communication or data transmission, to one or more client devices associated with at least one user to notify the at least one user that the geographical area includes the at least one flood risk geographical area. The method may include additional, less, or alternate actions, including those discussed elsewhere herein.

For example, the method may further include: (i) generating, via the at least one processor, a user list including the at least one user located in the geographical area, (ii) storing, via the at least one processor, in the at least one memory device, the received topography data from the at least one UV, (iii) receiving, via the at least one processor and/or associated transceiver, location data associated with the at least one flood risk geographical area, (iv) generating, via the at least one processor, a location of the at least one flood risk geographical area based upon the received location data, (v) receiving, via the at least one processor and/or associated transceiver, from a third party computing system, weather data associated with the location of the at least one flood risk geographical area, and/or (vi) determining, via the at least one processor, within the at least one flood risk geographical area, one or more areas being at an impending flood risk level based upon the weather data. Further, transmitting the alert may further comprise including a notification indicating the impending flood risk level of the one or more areas.

In yet another embodiment, a computer-implemented method for controlling and monitoring swimming pool water depth of a swimming pool may be provided. The method may be implemented via a computer system including at least one processor and/or associated transceiver in communication with at least one memory device and at least one sensor, and the method may include: (i) receiving, via the at least one processor and/or associated transceiver, water data from at least one sensor, wherein the water data is gathered by the at least one sensor located in a swimming pool, (ii) determining based upon the received water data, via the at least one processor, that the swimming pool is a flood risk swimming pool, wherein the flood risk swimming pool includes at least one of a threshold amount of water leaking from the swimming pool and a threshold amount of water overflowing the swimming pool, (iii) in response to determining that the swimming pool is a flood risk swimming pool, generating, via the at least one processor, an alert including information indicating that the swimming pool is a flood risk swimming pool, and/or (iv) transmitting, via the at least one processor and/or associated transceiver, the alert, via wireless communication or data transmission, to one or more client devices associated with at least one user of the swimming pool to notify the at least one user that the swimming pool is the flood risk swimming pool. The method may include additional, less, or alternate actions, including those discussed elsewhere herein.

For example, the alert may include at least one of a water leak alert, at risk of water overflowing alert, and a water overflowing alert. The method may further include: (i) storing in the at least one memory device, via the at least one processor, the received water data from the at least one sensor and/or (ii) transmitting, via the at least one processor and/or associated transceiver, draining instructions to a water depth controller of the swimming pool, wherein the draining instructions cause the water depth controller to drain the swimming pool.

Additional Considerations

As will be appreciated based upon the foregoing specification, the above-described embodiments of the disclosure may be implemented using computer programming or engineering techniques including computer software, firmware, hardware or any combination or subset thereof. Any such resulting program, having computer-readable code means, may be embodied or provided within one or more computer-readable media, thereby making a computer program product, e.g., an article of manufacture, according to the discussed embodiments of the disclosure. The computer-readable media may be, for example, but is not limited to, a fixed (hard) drive, diskette, optical disk, magnetic tape, semiconductor memory such as read-only memory (ROM), and/or any transmitting/receiving medium, such as the Internet or other communication network or link. The article of manufacture containing the computer code may be made and/or used by executing the code directly from one medium, by copying the code from one medium to another medium, or by transmitting the code over a network.

These computer programs (also known as programs, software, software applications, "apps", or code) include machine instructions for a programmable processor, and can be implemented in a high-level procedural and/or object-oriented programming language, and/or in assembly/machine language. As used herein, the terms "machine-readable medium" "computer-readable medium" refers to any computer program product, apparatus and/or device (e.g., magnetic discs, optical disks, memory, Programmable Logic Devices (PLDs)) used to provide machine instructions and/or data to a programmable processor, including a machine-readable medium that receives machine instructions as a machine-readable signal. The "machine-readable medium" and "computer-readable medium," however, do not include transitory signals. The term "machine-readable signal" refers to any signal used to provide machine instructions and/or data to a programmable processor.

As used herein, a processor may include any programmable system including systems using micro-controllers, reduced instruction set circuits (RISC), application specific integrated circuits (ASICs), logic circuits, and any other circuit or processor capable of executing the functions described herein. The above examples are example only, and are thus not intended to limit in any way the definition and/or meaning of the term "processor."

As used herein, the terms "software" and "firmware" are interchangeable, and include any computer program stored in memory for execution by a processor, including RAM memory, ROM memory, EPROM memory, EEPROM memory, and non-volatile RAM (NVRAM) memory. The above memory types are example only, and are thus not limiting as to the types of memory usable for storage of a computer program.

In one embodiment, a computer program is provided, and the program is embodied on a computer readable medium. In an exemplary embodiment, the system is executed on a single computer system, without requiring a connection to a sever computer. In a further embodiment, the system is being run in a Windows® environment (Windows is a registered trademark of Microsoft Corporation, Redmond, Wash.). In yet another embodiment, the system is run on a mainframe environment and a UNIX® server environment (UNIX is a registered trademark of X/Open Company Limited located in Reading, Berkshire, United Kingdom).

The application is flexible and designed to run in various different environments without compromising any major functionality.

In some embodiments, the system includes multiple components distributed among a plurality of computer devices. One or more components may be in the form of computer-executable instructions embodied in a computer-readable medium. The systems and processes are not limited to the specific embodiments described herein. In addition, components of each system and each process can be practiced independent and separate from other components and processes described herein. Each component and process can also be used in combination with other assembly packages and processes. The present embodiments may enhance the functionality and functioning of computers and/or computer systems.

As used herein, an element or step recited in the singular and preceded by the word "a" or "an" should be understood as not excluding plural elements or steps, unless such exclusion is explicitly recited. Furthermore, references to "exemplary embodiment," "exemplary embodiment," or "one embodiment" of the present disclosure are not intended to be interpreted as excluding the existence of additional embodiments that also incorporate the recited features.

Furthermore, as used herein, the term "real-time" refers to at least one of the time of occurrence of the associated events, the time of measurement and collection of predetermined data, the time for a computing device (e.g., a processor) to process the data, and the time of a system response to the events and the environment. In the embodiments described herein, these activities and events occur substantially instantaneously.

The patent claims at the end of this document are not intended to be construed under 35 U.S.C. § 112(f) unless traditional means-plus-function language is expressly recited, such as "means for" or "step for" language being expressly recited in the claim(s).

This written description uses examples to disclose the disclosure, including the best mode, and also to enable any person skilled in the art to practice the disclosure, including making and using any devices or systems and performing any incorporated methods. The patentable scope of the disclosure is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

We claim:

1. A computer system for detecting environmental pollution levels in a water source and alerting users in real-time of the environmental pollution levels within the water source, the computer system including at least one processor in communication with at least one memory device and at least one sensor, the at least one processor programmed to:
   receive pollution data from at least one sensor, wherein the pollution data is gathered by the at least one sensor located at a water source;
   determine a level of environmental pollution in the water source based upon the received pollution data;
   determine, based upon the analysis of the pollution data, whether the water source is polluted;
   in response to determining that the water source is polluted, generate an alert including information corresponding to the polluted water source;
   generate a user list including at least one user of the water source;
   transmit the alert, via wireless communication or data transmission, to one or more client devices associated with the at least one user to notify the at least one user that the water source is polluted;
   generate a safe water source list including a location of at least one safe water source, wherein the at least one safe water source is not the polluted water source; and
   in response to determining that the at least one user is travelling to the at least one safe water source, determine that the at least one user requires water commodity insurance coverage.

2. The computer system of claim 1, wherein the alert is at least one of a water quality alert and a boil water order.

3. The computer system of claim 1, wherein the at least one processor is further programmed to:
   receive location data associated with the at least one user;
   compare the received location data associated with the at least one user and the location of the at least one safe water source; and
   determine, based upon the comparison, whether the at least one user is travelling to the at least one safe water source.

4. The computer system of claim 1, wherein the at least one processor is further programmed to:
   store, in the at least one memory device, the received pollution data from the at least one sensor; and
   store, in the at least one memory device, the user list including the at least one user of the polluted water source.

5. A computer-implemented method for detecting environmental pollution levels in a water source and alerting users in real-time of the environmental pollution levels within the water source, the method being implemented via a computer system including at least one processor and/or associated transceiver in communication with at least one memory device and at least one sensor, the method comprising:
   receiving, via the at least one processor and/or associated transceiver, pollution data from at least one sensor, wherein the pollution data is gathered by the at least one sensor located at a water source;
   determining, via the at least one processor, a level of environmental pollution in the water source based upon the received pollution data;
   determining, via the at least one processor, based upon the analysis of the pollution data, whether the water source is polluted;
   in response to determining that the water source is polluted, generating, via the at least one processor, an alert including information corresponding to the polluted water source;
   generating, via the at least one processor, a user list including at least one user of the water source;
   transmitting, via the at least one processor and/or associated transceiver, the alert, via wireless communication or data transmission, to one or more client devices associated with the at least one user to notify the at least one user that the water source is polluted;
   generating, via the at least one processor, a safe water source list including a location of at least one safe water source, wherein the at least one safe water source is not the polluted water source; and
   in response to determining that the at least one user is travelling to the at least one safe water source, determining, via the at least one processor, that the at least one user requires water commodity insurance coverage.

6. The computer-implemented method of claim 5, wherein the alert is at least one of a water quality alert and a boil water order.

7. The computer-implemented method of claim 5, the method further comprising:
  receiving, via the at least one processor and/or associated transceiver, location data associated with the at least one user;
  comparing, via the at least one processor, the received location data associated with the at least one user and the location of the at least one safe water source; and
  determining based upon the comparison, via the at least one processor, whether the at least one user is travelling to the at least one safe water source.

8. The computer-implemented method of claim 5, the method further comprising:
  storing in the at least one memory device, via the at least one processor, the received pollution data from the at least one sensor; and
  storing in the at least one memory device, via the at least one processor, the user list including the at least one user of the polluted water source.

* * * * *